US012161808B2

(12) United States Patent
Barraclough et al.

(10) Patent No.: US 12,161,808 B2
(45) Date of Patent: Dec. 10, 2024

(54) USER INTERFACE FOR SUPPLYING GASES TO AN AIRWAY

(71) Applicant: Fisher & Paykel Healthcare Limited, Auckland (NZ)

(72) Inventors: Michael Robert Barraclough, Auckland (NZ); Matthew Jon Payton, Auckland (NZ); Callum James Thomas Spence, Auckland (NZ); Laurence Gulliver, Auckland (NZ); Samantha Dale Oldfield, Auckland (NZ); Dexter Chi Lun Cheung, Auckland (NZ); Geraldine Frances Keogh, Auckland (NZ); Milanjot Singh Assi, Auckland (NZ); Alicia Jerram Hunter Evans, Auckland (NZ); Craig Karl White, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 0 days.

(21) Appl. No.: 17/672,104

(22) Filed: Feb. 15, 2022

(65) Prior Publication Data

US 2022/0323704 A1 Oct. 13, 2022

Related U.S. Application Data

(63) Continuation of application No. 15/562,127, filed as application No. PCT/NZ2016/050054 on Mar. 31, 2016, now Pat. No. 11,298,494.

(Continued)

(51) Int. Cl.
*A61M 16/06* (2006.01)
*A61M 16/00* (2006.01)
(Continued)

(52) U.S. Cl.
CPC .... *A61M 16/0666* (2013.01); *A61M 16/0434* (2013.01); *A61M 16/0493* (2014.02);
(Continued)

(58) Field of Classification Search
CPC ... A61M 16/0666–0694; A61M 16/049–0495; A61J 17/001
See application file for complete search history.

(56) References Cited

U.S. PATENT DOCUMENTS 3,974,828 A 8/1976 Bird
4,535,767 A 8/1985 Tiep
(Continued)

FOREIGN PATENT DOCUMENTS

GB 2368533 5/2002
WO WO 2003/041780 5/2003
(Continued)

OTHER PUBLICATIONS

Australian Government, Examination Report No. 1, Application No. 2016241100, dated Dec. 2, 2019, 3 pages.
(Continued)

*Primary Examiner* — Joseph D. Boecker
*Assistant Examiner* — Thomas W Greig
(74) *Attorney, Agent, or Firm* — Knobbe Martens Olson & Bear LLP

(57) ABSTRACT

A user interface convertible between a nasal configuration and an oral configuration. The user interface has a nasal cannula and a mouthpiece. The nasal cannula has a body portion and at least one prong extending from the body portion, the prong being adapted to direct a flow of gas into a nare of a user's nose. The mouthpiece is adapted to engage the mouth of the patient and direct a flow of gas into a user's mouth. In the nasal configuration the prong of the nasal cannula is adapted to direct a flow of gases into a nare of the (Continued)

patient. In the oral configuration, the nasal cannula is engaged with the mouthpiece such that a gases flow is provided to at least the mouth of the user.

17 Claims, 20 Drawing Sheets

Related U.S. Application Data

(60) Provisional application No. 62/140,638, filed on Mar. 31, 2015, provisional application No. 62/140,853, filed on Mar. 31, 2015, provisional application No. 62/140,659, filed on Mar. 31, 2015.

(51) Int. Cl.
*A61M 16/04* (2006.01)
*A61M 16/08* (2006.01)
*A61M 16/20* (2006.01)

(52) U.S. Cl.
CPC ........ *A61M 16/0495* (2014.02); *A61M 16/06* (2013.01); *A61M 16/0672* (2014.02); *A61M 16/0683* (2013.01); *A61M 16/0816* (2013.01); *A61M 16/201* (2014.02); *A61M 16/209* (2014.02); *A61M 2016/0027* (2013.01)

(56) References Cited

U.S. PATENT DOCUMENTS

| | | | |
|---|---|---|---|
| 4,821,709 A | | 4/1989 | Jensen |
| 5,375,593 A * | | 12/1994 | Press ................. A61M 16/0666 128/207.18 |
| 6,192,884 B1 | | 2/2001 | Vann et al. |
| 6,581,599 B1 | | 6/2003 | Stenzler |
| 7,105,008 B2 | | 9/2006 | Maryanka |
| 8,741,220 B2 * | | 6/2014 | O'Donnell .......... A61M 16/024 128/203.14 |
| 8,910,635 B2 * | | 12/2014 | Pierro ................. A61M 16/085 128/206.28 |
| 9,474,873 B2 * | | 10/2016 | Zhang ................ A61M 16/0493 |
| 9,981,102 B2 * | | 5/2018 | Veliss ............... A61M 16/0683 |
| 11,298,494 B2 * | | 4/2022 | Barraclough ..... A61M 16/0672 |
| 2002/0053286 A1 | | 5/2002 | Czabala |
| 2003/0094178 A1 | | 5/2003 | McAuley et al. |
| 2005/0028816 A1 | | 2/2005 | Fishman et al. |
| 2005/0028822 A1 | | 2/2005 | Sleeper et al. |
| 2005/0217671 A1 | | 10/2005 | Fisher et al. |
| 2006/0042631 A1 | | 3/2006 | Martin et al. |
| 2006/0174889 A1 | | 8/2006 | Noble |
| 2006/0207597 A1 | | 9/2006 | Wright |
| 2008/0047559 A1 | | 2/2008 | Fiori |
| 2008/0051674 A1 | | 2/2008 | Davenport et al. |
| 2008/0190436 A1 * | | 8/2008 | Jaffe ................. A61M 16/0688 128/207.18 |
| 2009/0114229 A1 * | | 5/2009 | Frater ............... A61M 16/0683 128/205.25 |
| 2009/0151719 A1 | | 6/2009 | Wondka et al. |
| 2011/0125052 A1 | | 5/2011 | Davenport et al. |
| 2011/0315143 A1 * | | 12/2011 | Frater ............... A61M 16/0616 128/206.28 |
| 2012/0017909 A1 | | 1/2012 | Porges et al. |
| 2012/0240924 A1 | | 9/2012 | Rustad |
| 2013/0160766 A1 | | 6/2013 | Malouf et al. |
| 2013/0199537 A1 * | | 8/2013 | Formica ............ A61M 16/0816 128/205.25 |
| 2013/0340752 A1 | | 12/2013 | Landis et al. |
| 2014/0290668 A1 * | | 10/2014 | Thornton ............ A61M 16/049 433/213 |
| 2018/0071469 A1 | | 3/2018 | Oldfield et al. |
| 2018/0078726 A1 | | 3/2018 | Barraclough et al. |

FOREIGN PATENT DOCUMENTS

| | | |
|---|---|---|
| WO | WO 2007/063532 | 6/2007 |
| WO | WO 2008/092021 | 7/2008 |
| WO | WO 2009/123977 | 10/2009 |
| WO | WO 2012/040792 | 4/2012 |
| WO | WO 2015/049538 | 4/2015 |

OTHER PUBLICATIONS

European Patent Office, Communication Pursuant to Article 94(3) EPC, Application No. 16 773 542.2-1122, dated Oct. 7, 2020, in 4 pages.
European Patent Office, Examination Report; Application No. 16 773 524.2-1122, dated Nov. 22, 2019, 4 pages.
European Patent Office, Examination Report; Application No. 16 773 524.2-1122, dated Oct. 10, 2020, 4 pages.
European Search Report in EP Application No. 16773542.2 dated Oct. 17, 2018 in 6 pages.
International Search Report; PCT/IB2015/051818, filed Mar. 31, 2016, dated Jul. 27, 2016.
International Search Report; PCT/NZ2016/050054; dated May 27, 2016, 5 pages.
Second Australian Examination Report; Application No. 2016241100, dated Nov. 25, 2020, 5 pages.

\* cited by examiner (a)   (b)

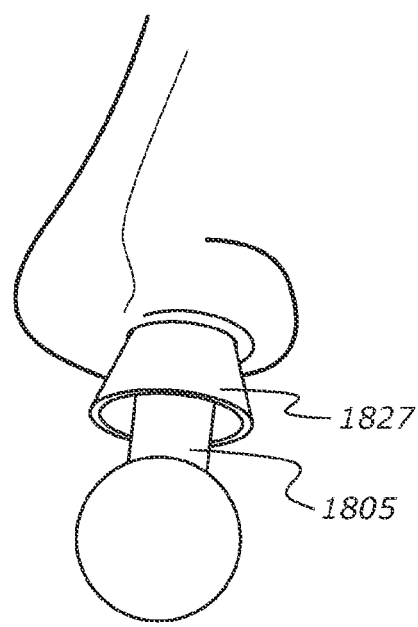
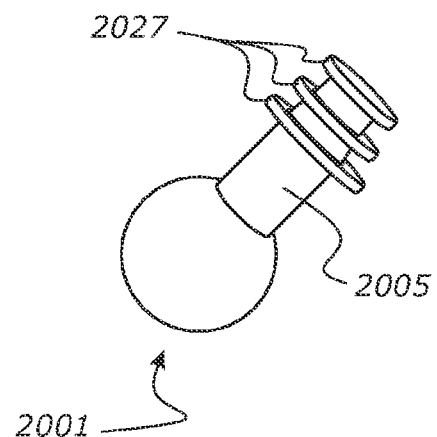
FIGURE 19
FIGURE 20
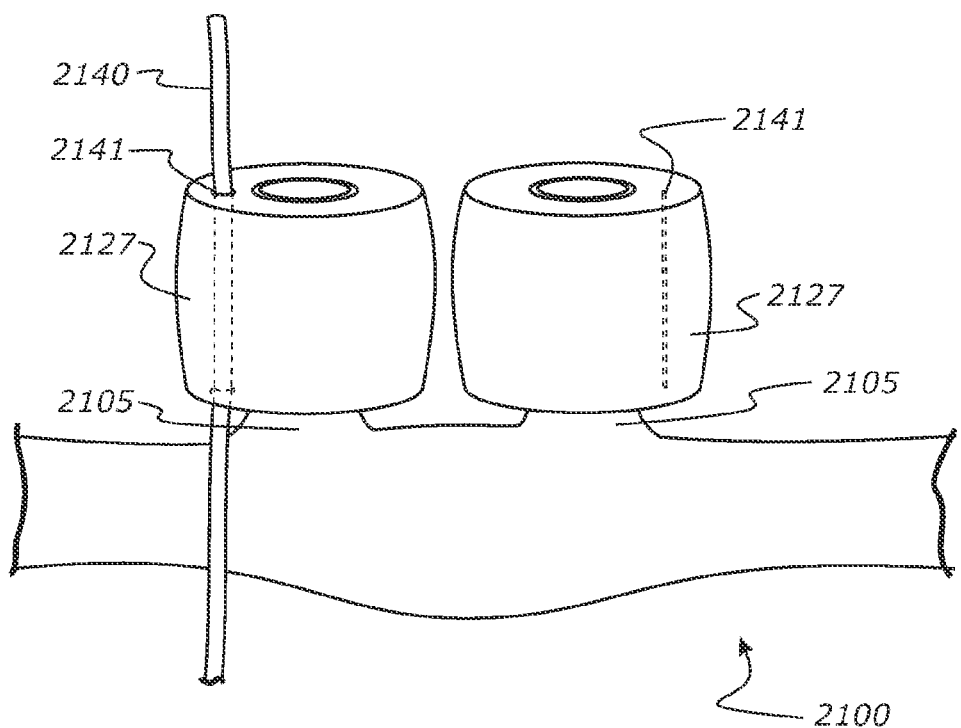
FIGURE 21

USER INTERFACE FOR SUPPLYING GASES TO AN AIRWAY

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

TECHNICAL FIELD

The present disclosure relates to user interfaces for medical circuits for conveying gases to and/or from a user.

BACKGROUND ART

Patients may lose respiratory function during anaesthesia, or sedation, or more generally during certain medical procedures. Prior to a medical procedure a patient may be pre-oxygenated by a medical professional to provide a reservoir of oxygen saturation, and this pre-oxygenation is generally carried out with a bag and a face mask. Once under general anaesthesia, patients must be intubated to ventilate the patient. In some cases, intubation is completed in 30 to 60 seconds, but in other cases, particularly if the patient's airway is difficult to traverse (for example, due to cancer, severe injury, obesity or spasm of the neck muscles), intubation will take significantly longer. While pre-oxygenation provides a buffer against declines in oxygen saturation, for long intubation procedures, it is necessary to interrupt the intubation process and reapply the face mask to increase the patient's oxygen saturation to adequate levels. The interruption of the intubation process may happen several times for difficult intubation processes, which is time consuming and puts the patient at severe health risk. After approximately three attempts at intubation the medical procedure will be abandoned.

In this specification where reference has been made to patent specifications, other external documents, or other sources of information, this is generally for the purpose of providing a context for discussing the features of the disclosure. Unless specifically stated otherwise, reference to such external documents is not to be construed as an admission that such documents, or such sources of information, in any jurisdiction, are prior art, or form part of the common general knowledge in the art.

SUMMARY

It is an object of the present disclosure to provide an interface that will at least go some way towards improving on the above or which will at least provide the public and the medical profession with a useful choice.

The interface system may be configured to deliver general anaesthetic to the user via the aperture or the port of the user interface, while separately or in addition, also to deliver a high flow of oxygen to the nares of the user via the nasal cannula.

Other drugs or agents or medicaments or gases delivery is also contemplated. Anesthesia delivery is one example provided in this specification to give context to the present interface system, and it will be appreciated other delivery of medicament/drugs or gases can be provided through the systems and devices disclosed herein.

In accordance with at least one of the embodiments disclosed herein is a patient interface comprising a combination of an oro-nasal mask and a nasal cannula assembly, each of said mask and nasal cannula assembly provided with separate gas flow supply from one or more sources, said nasal cannula being independently locatable upon a user from said mask.

In accordance with an aspect of the invention, there is provided a user interface convertible between a nasal configuration and an oral configuration, the user interface comprising: a nasal cannula having a body portion, at least one prong extending from the body portion, the prong being adapted to direct a flow of gas into a nare of a user's nose, a mouthpiece adapted to engage the mouth of the patient and direct a flow of gas into a user's mouth, in the nasal configuration the prong of the nasal cannula is adapted to direct a flow of gases into a nare of the patient, and in the oral configuration, the nasal cannula is engaged with the mouthpiece such that a gases flow is provided to at least the mouth of the user.

The user interface may be further convertible into an oro-nasal configuration.

The user interface may further comprise a gas delivery conduit, and a valve between the nasal cannula and the mouthpiece, wherein in the nasal configuration, the gas delivery conduit delivers a flow of gas to the nasal cannula and the valve prevents or substantially inhibits a flow of gas between the nasal cannula and the mouthpiece, in the oral configuration, the gas delivery conduit delivers a flow of gas to the mouthpiece and the valve prevents or substantially inhibits a flow of gas between the nasal cannula and the mouthpiece, and in the oro-nasal configuration, the gas delivery conduit delivers a flow of gas to the mouthpiece or the nasal cannula and the valve allows a flow of gas between the nasal cannula and the mouthpiece.

The mouthpiece may be clipable onto the cannula.

The gas delivery conduit may be attachable to either the nasal cannula or to the mouthpiece, and the gas delivery conduit is moveable between the nasal cannula and the mouthpiece.

The valve may be or comprise a flap valve that seals either the nasal cannula or the mouthpiece from the other of the mouthpiece or nasal cannula that is receiving flow from the gas delivery conduit.

The mouthpiece may comprise an opening adapted to receive and allow instruments to be inserted through the mouthpiece, the mouthpiece further comprising a valve or seal to seal around the mouthpiece opening.

The mouthpiece may be adapted to surround at least a portion of the cannula and the mouth piece has an outer periphery that substantially conforms to the area of a patient's mouth, such that in use at least a portion of the mouth is at least partially occluded.

The mouth piece may be slidable relative to the cannula.

In the oral configuration the mouthpiece may be insertable into the mouth of the user such that the at least one prong of the nasal cannula provide a gases flow to the mouth of the patient.

The mouthpiece may be inflatable such that the mouthpiece at least partially occludes or at least partially seals with the mouth of the user.

The mouthpiece may comprise an inflatable cuff, the cuff adapted to conform to the shape of the mouth to create a seal with the mouth.

The prongs may be configured to at least partially occlude or at least partially seal with the user's nares, in use.

The prongs may be inflatable.

The mouthpiece may comprise an extended section that is adapted to extend into the airway of the patient and lie over the top of the tongue of the user.

In accordance with an aspect of the invention, there is provided a user interface for providing a flow of respiratory gases to a patient during a medical procedure comprising a nasal interface comprising a body and a pair of prongs extending from the body, the prongs configured to engage nares of the patient's nose and direct high flow respiratory gases into the nares a mouthpiece adapted to engage the mouth of the patient; and wherein the prongs and/or the mouthpiece are configured to at least partially occlude either an oral airway, a nasal passage, or both the oral airway or nasal passage in use.

The user interface may be configured to create at least a partial seal with the nares of the patient.

The user interface may be configured to create at least a partial seal with the mouth/oral airway of the user.

The user interface may be adapted to allow a user to selectively create at least a partial occlusion with the nares of the user/patient or with the oral airway/mouth or with both.

The user interface may be shaped to create a seal with the nares of the user.

The user interface may be shaped to create a seal with the user's mouth or oral airways.

The user interface may be arranged to direct high flow respiratory gases into the mouth/oral airways of the patient.

The user interface may be inflatable to create at least a partial seal with the nares of the patient.

The mouthpiece may be inflatable to create at least a partial seal with the mouth of the patient.

The user interface may further comprise a mechanical control mechanism that allows selective inflation of the prongs, the mouth piece, or both the prongs and the mouthpiece.

Each prong may be independently inflatable to create at least a partial seal with the nares of the patient.

Nasal interface may be removably connectable to the mouthpiece.

The mouthpiece may be inflatable when the nasal interface is connected to the mouthpiece.

The mouthpiece may comprise a passage to allow insertion of a medical instrument through the mouthpiece, the mouthpiece may be shaped to conform to the shape of a patient's mouth to create a seal with the mouth.

The passage is selectively openable and closeable to seal around the medical instrument inserted through the mouthpiece.

The passage may comprise a passage inflatable seal, the passage inflatable seal being adapted to seal around a medical instrument inserted into the passage.

The mouthpiece may comprise an outer inflatable seal that is adapted to inflate to create a seal with the mouth of the patient.

The user interface may further comprise a seal activation mechanism controlling the inflation and deflation of the prongs and/or the mouthpiece.

The user interface may further comprise a valve that can be selectively opened or closed based on the patient's inspiration and expiration.

The mouthpiece may comprise a pressure line, the pressure line includes a cover slip that is moveable within the pressure line, the movement of the cover slip controlling opening and closing of the valve, the cover slip configured to move to open the valve during inspiration and the cover slip configured to move to close the valve during expiration.

In accordance with an aspect of the invention, there is provided a mouthpiece for use in medical procedures comprising: a body, the body including an opening to allow insertion of a medical instrument and being configured to create a seal with the mouth of the patient to increase pressure in the airways of the patient.

The mouthpiece may further comprise an inflatable cuff disposed on the body of the mouthpiece, the inflatable cuff creating a seal with the patient's mouth when inflated.

The mouthpiece may comprise an opening seal for sealing around the opening to retain the medical instrument.

The user interface may be a bite-block having a passage which can be selectively opened or closed.

Disclosed is a patient interface comprising at least one delivery element for delivering or directing a flow of supplied gas to a nare or the nares of a user's nose, wherein each delivery element comprises of at least one lumen through which said flow of supplied gas is directed, and wherein the flow of supplied gas is modified according to one or more forms is provided within or about an interior of one or more of said at least one lumen.

Said form may be a, or one more, surface relief portions or regions provided as part of an internal wall surface of one or more of said at least one lumen.

Said form may be a projection extending radially inwardly from or along an interior wall surface of one or more of said at least one lumen.

Said form may be a depression or recess provided within or along a portion or region of an interior wall surface of one or more of said at least one lumen.

Said form may extend in a continuous or discontinuous manner along or about the delivery element, from a downstream location to a more upstream location, said location being relative to the direction of the flow of suppled gas through said delivery element.

Said form may comprise one or more partitions extending along a length and/or across a cross-sectional area of the at least one lumen of a said delivery element.

Said form may be one or more partitions arranged or arrayed in one or a combination of the following:
  substantially concentric configurations, each of said partitions defining at least a part of a further one of said at least one lumen, whether said partitions define a lumen that extends substantially the entirety of the length, or a partial length, of the total length of a delivery element through which said flow of supplied gas is directed,
  a hexagonal or honey-comb type configuration of partitions, whether said partitions defines at least a part of a further one of said at least one lumen, or whether said partitions define a lumen that extends substantially the entirety of the length, or a partial length, of the total length of a delivery element through which said flow of supplied gas is directed,
  a cross-hatch or grid-type arrangement of partitions when viewed as a cross-section through the gas delivery element, the cross-section being taken as a substantially orthogonal plane relative to the direction of the flow supplied gas through the gas delivery element,
  a plurality of intersecting partitions providing plurality of divisions or dividing interior walls within at least one of said lumen of said delivery element,
  a plurality of intersecting partitions providing for a plurality of separate gas flow pathways within at least one of said lumen of a said delivery element,
  one or more partitions are vanes interposed within one or more lumen of said delivery element, combinations of one or more of the above arrangements or arrays.

Said form may be one or more partitions, a partition being a dividing wall or structure extending through or across a delivery element for gas flow modification or gas flow re-direction.

Said form may impose upon the flow of gas through one or more regions of one or more delivery elements.

Said form may impose upon the flow of gas through one or more regions of one or more delivery elements to modify the gas flow by reducing or increasing the Reynolds number of the flow of gas, or at least portions of the flow of gas, through one or more regions of the delivery element.

Said form may impose upon the flow of gas to increase, or decrease, the kinetic energy of a bulk of the gas flow through the delivery element, or a localised or partial portion of the gas flow through the delivery element.

Said form may comprise a helical structure or surface relief extending from, or imposed upon, an interior wall portion of said at least one lumen of one or more gas delivery elements.

Said form may comprise striations.

Said striations may be oriented along or with or against a flow direction of supplied gas through a gas delivery element.

One or more of said form(s) may be located in one or more of:
  in a portion or region closer to an outlet from the delivery element than an inlet of the supplied gases to the delivery element,
  in a portion or region closer to an inlet to the delivery element than an outlet of the supplied gases from the delivery element,
  in a portion or region comparatively more downstream than an upstream portion or region of a delivery element relative the flow of gas supplied,
  in a portion or region comparatively more upstream than a downstream portion or region of a delivery element relative the flow of gas supplied, at or substantially adjacent to an outlet (or an end) from the delivery element of the supplied gases,
  an outlet end of the delivery element,
  an outlet end of said delivery element may comprise the form as one or a serried of serrated surfaces or undulating shaped or castellated edge portions.

Said form may be one or more ribs provided substantially longitudinally aligned with a gas flow direction through the delivery element, or said one or more ribs is/are provided substantially laterally (or another orientation) substantially relative to a gas flow direction through the delivery element.

Said form may be of a regular or irregular geometry, when viewed as a cross-sectional profile or as plan view of a surface of a delivery element including such a said form or forms.

The, or one or more of said, form(s) may be gas flow directors.

A said form may straighten or direct the gas flow into a flow path trajectory or other gas flow characteristic.

Said form may straighten said gas flow or provides or alters said gas flow as a jet or focused flow of gas through or from said delivery element or through or from at least one of said lumen through a delivery element.

Said form may operate as a gas flow multiplier for increasing the flowrate of provided to a user, the gas flowrate provided to a user being greater than the total gas flowrate delivered through the delivery element of a said interface.

Said delivery element may be oriented or angled, such that in-use, said delivery element may be oriented or angled toward a user's septum.

Said delivery element may extend to, or substantially adjacent to, in-use, one of:
  a user's nasal valve
  the velopharynx
  sufficiently deep into a user's airway or nasal cavity, so s to in-use, avoid or by-pass gas flow being provided in contact with a user's relatively sensitive nasal epithelia.

A delivery element may extend in flow path length, whether automatically in response to a characteristic of the supplied gas or by manually actuation.

Said delivery element may be telescopic.

Said delivery element responds to a change in temperature or a change in humidity or an electrical current applied thereto.

Said response may be an alteration or change in the geometry or flow path of a said delivery element.

An outlet from a delivery element may be shaped or configured to change the velocity of gas exiting said delivery element.

Said velocity (whether as a bulk property or a localised property of said supplied gas passing through or exiting a said delivery element) may be increased or decreased.

Said form may be a flow restrictor.

Said delivery element may be of a non-sealing type relative to an airway or a nasal cavity or nare into which said delivery element is to be located, optionally such that the nare or airway that said delivery element may be to be located within does not occlude the entire airway or a nare when in-situ.

Said delivery element may further comprise one or more structures positioned on an exterior surface of said delivery element, such that, in-use, said a sealing of said delivery element with an airway or a nare when in-use, is dissuaded or avoided or prevented.

Said delivery element may be of a sealing-type, optionally wherein the delivery element occludes or seals the airway or nare when in-situ.

Said delivery element may further comprise one or more structures positioned on an exterior surface of said delivery element, such that, in-use, said a sealing of said delivery element with an airway or a nare when in-use, is encouraged.

Said structure(s) may comprise one or more inflatable members for encouraging of said sealing, optionally said member being at least one inflatable cuff.

The inflatable member may be inflated to a pressure proportional to the pressure of the supplied gas or to a pressure correlated to the pressure of the supplied gas.

Said inflatable member may be inflated by the supplied gas.

Said inflatable member may be inflated by a source of gas other than the supplied gas.

The inflatable member may be manually inflated by a user, or may be automatically inflated, such as in response to a supplied source of gas.

Said delivery element may further comprise an accommodation to allow for insertion of an instrument or tube or conduit or other airway equipment, including a bougie, into a said delivery element to access a user's airway, such as a nasal cavity or nare.

Said delivery element may be a nasal prong.

Said interface may be a nasal cannula including one or a pair of nasal prongs.

In some configurations, there is provided as a nasal cannula comprising one or a pair of nasal prongs as said delivery elements, in combination with a further patient interface when provided as an oro-nasal or full-face type mask, optionally each of said patient interfaces supplied separately with a source of gas to their gas outlet from respective delivery elements.

The or an interface or a component associated with a system for providing a supply of gas to said interface, may include a pressure relief mechanism.

The pressure relief mechanism may be a valve or other seal configured to open once a pre-determined pressure is experienced or sensed within a delivery element or at a location along a gas flow path of the gas supplied to the interface or a said gas delivery element, or said pre-determined pressure is measured or sensed at another location external to the interface of the system for providing the supply of gas.

It is an object of certain embodiments disclosed herein to provide an improved patient interface or systems or devices associated with patient interfaces that might solve one or more of the above problems, or at least provide the public with a useful choice.

As relatively high gas delivery flow rates may be used with the embodiments or configurations described herein, the gases being supplied or delivered to the user or patient may be delivered to different parts of the user's or a patient's airway. The gases being supplied may reach the patient's lungs or any part of the respiratory system.

For example, according to those various embodiments and configurations described herein, a flow rate of gases supplied or provided to an interface or via a system, such as through a flow path, may comprise, but is not limited to, flows of at least about 5, 10, 20, 30, 40, 50, 60, 70, 80, 90, 100, 110, 120, 130, 140, or 150 liters per min (LPM), or more, and useful ranges may be selected between any of these values (for example, about 40 to about 80, about 50 to about 80, about 60 to about 80, about 70 to about 80 LPM). Optionally, the gases supplied may be delivered in a fully saturated or humidified condition, or a saturated or humidified gas may be blended with other gases for supply or delivery to a patient interface or the patient.

Such relatively high flow rates of gases may assist in providing the supplied gases into a user's airway, or to different parts of a user's airway, for example such flow rates may allow for a delivery of such gases to the upper or lower airway regions. Upper airway region typically includes the nasal cavity, pharynx and larynx, while the lower airway region typically includes the trachea, primary bronchi and lungs.

Each of the various configurations or embodiments or configurations described herein may be utilised in combination with one or more of the other various systems, devices (including interfaces) or methods also described herein.

The term "comprising" as used in this specification means "consisting at least in part of". When interpreting each statement in this specification that includes the term "comprising", features other than that or those prefaced by the term may also be present. Related terms such as "comprise" and "comprises" are to be interpreted in the same manner.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting. Where specific integers are mentioned herein which have known equivalents in the art to which this invention relates, such known equivalents are deemed to be incorporated herein as if individually set forth.

BRIEF DESCRIPTION OF THE DRAWINGS

Preferred embodiments of the disclosure will be described by way of example only and with reference to the drawings, in which.

Figure 9A:
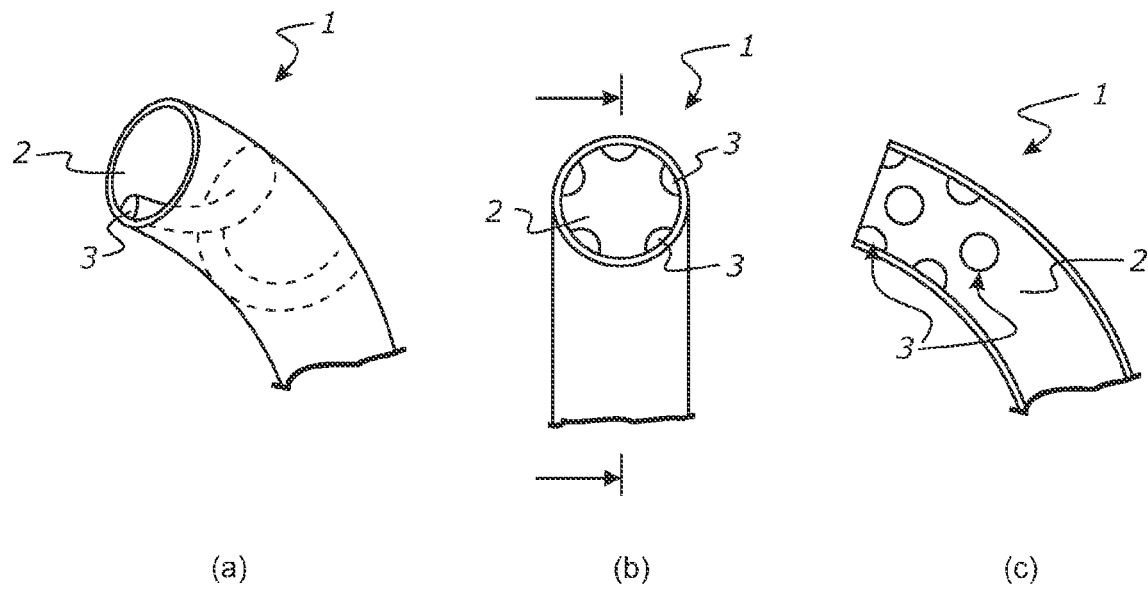

With respect to each of FIG. 9A parts (a), (b) and (c)—these show variations of a delivery element that includes a form to be imposed upon a gas flow through the lumen of the delivery element.

Figure 9B:
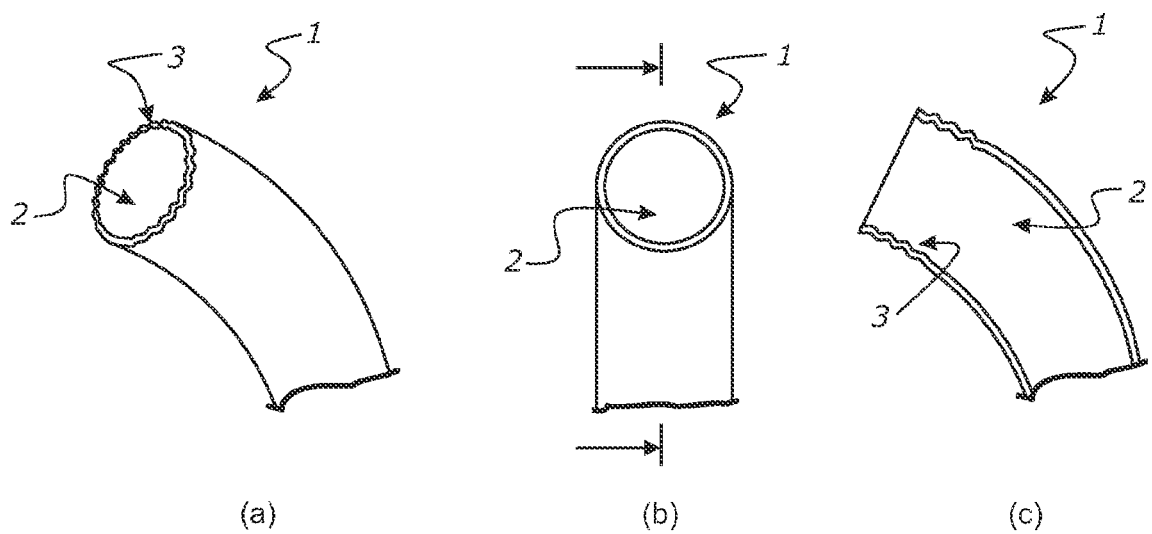

With respect to each of FIG. 9B parts (a), (b) and (c)—these show further variations of a delivery element that includes a form to be imposed upon a gas flow flowing through a delivery element.

Figure 10A:
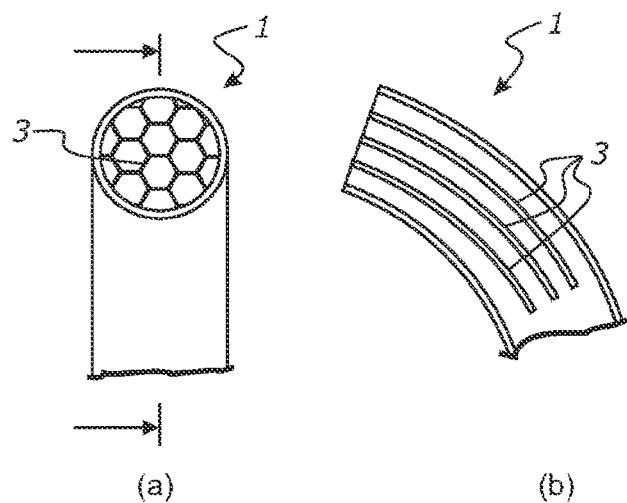

FIGS. 10A (a) and (b) show different views of a delivery element in which a honey-comb-like arrangement of forms are provided within the lumen of a delivery element.

Figure 10B:
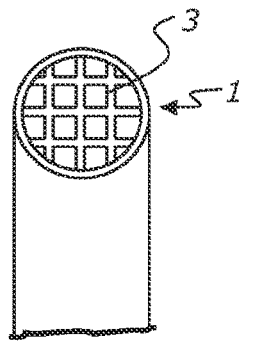

FIG. 10B shows a delivery element with a grid-like or mesh-like arrangement of forms.

Figure 10C:
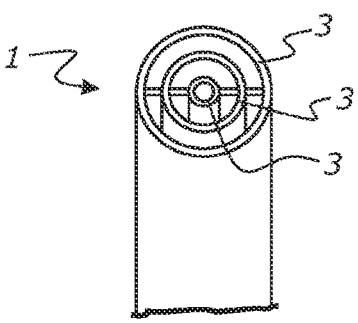

FIG. 10C shows a delivery element including an array of concentrically arranged forms, including additional forms for dividing or partitioning of the delivery element.

Figure 11:
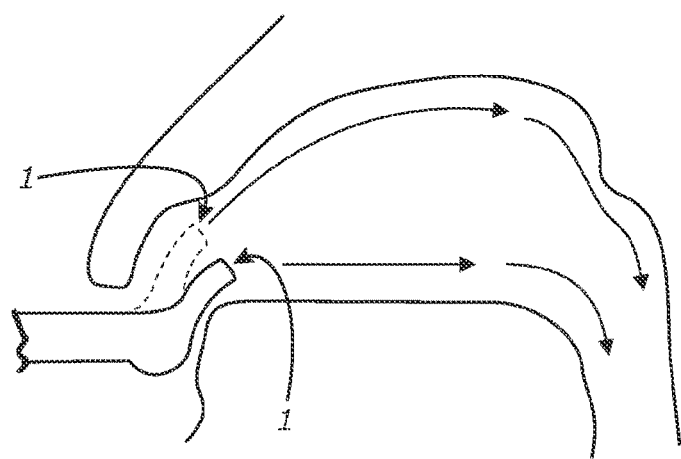

FIG. 11 shows a configuration in which multiple delivery elements provided in an airway, such as a pair of nasal prongs provided in a single nostril, and may be orientated.

Figure 12:
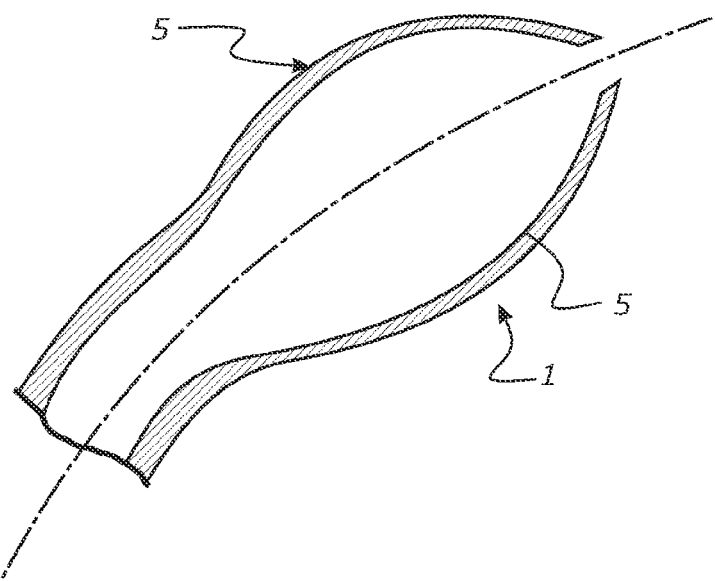

FIG. 12 shows a configuration of a delivery element in which wall sections of a nasal prong may be subject to ballooning when under pressure from the gas flowing therethrough, or the walls may be relatively thin to allow for such change in shape of the delivery element.

Figure 13:
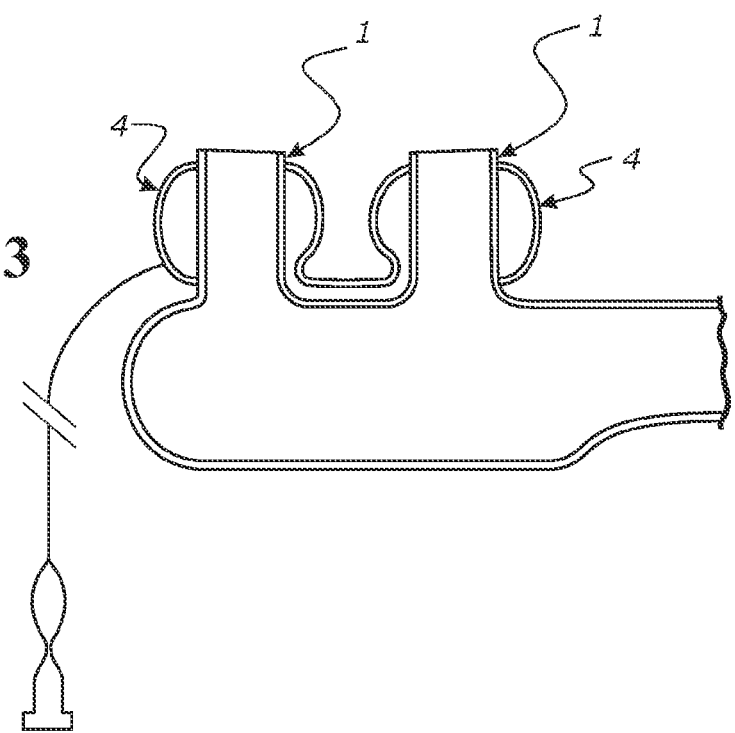

FIG. 13 shows a general patient interface, with a pair of delivery elements as nasal prongs including inflatable members as inflatable cuffs about the exterior surface of the delivery element.

Figure 14A:
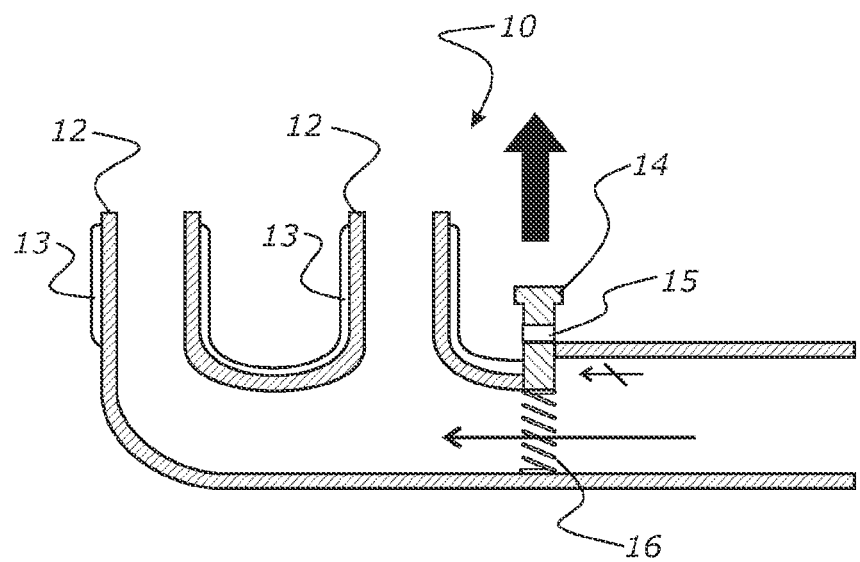
Figure 14B:
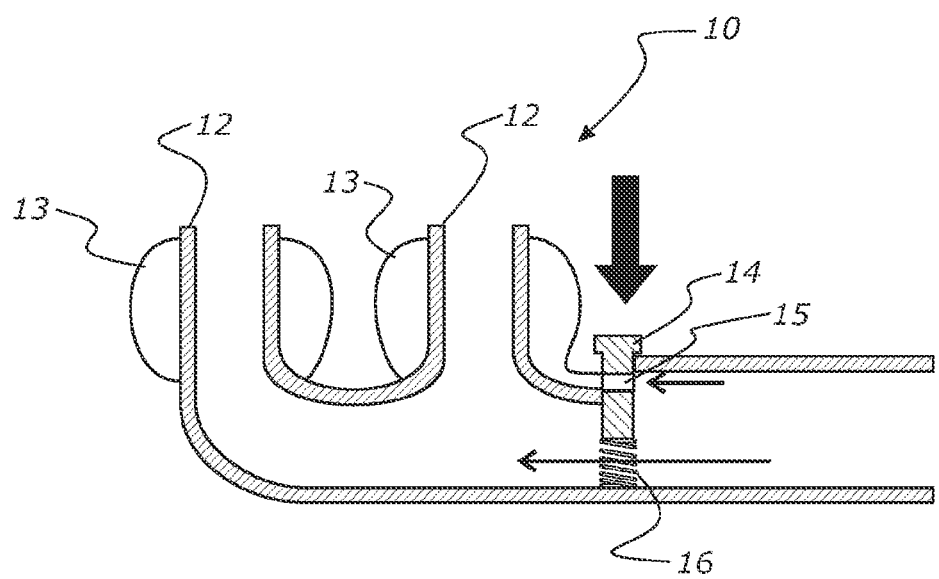

FIGS. 14A and 14B show a first embodiment of a user interface which comprises a selectively activated seal.

Figure 15A:
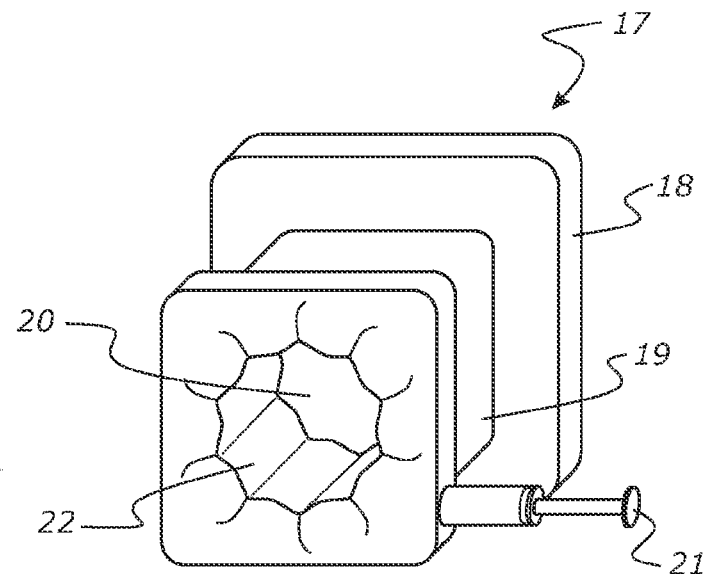
Figure 15B:
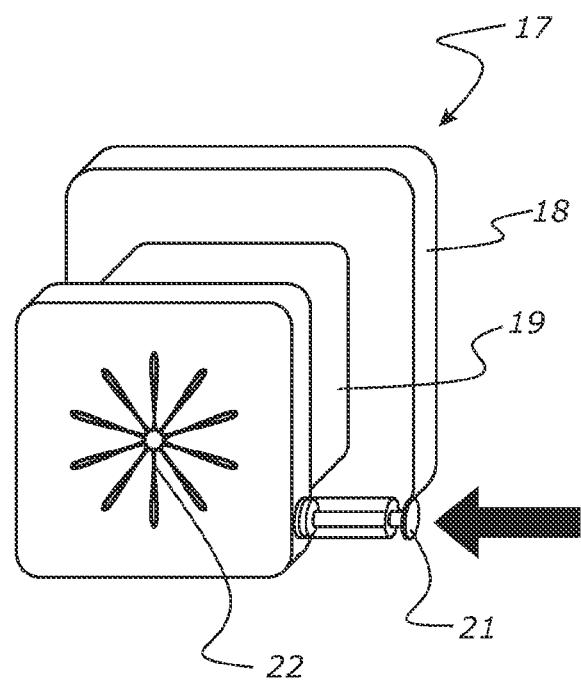

FIGS. 15A and 15B show a second embodiment of a user interface which comprises a selectively activated seal.

Figure 16A:
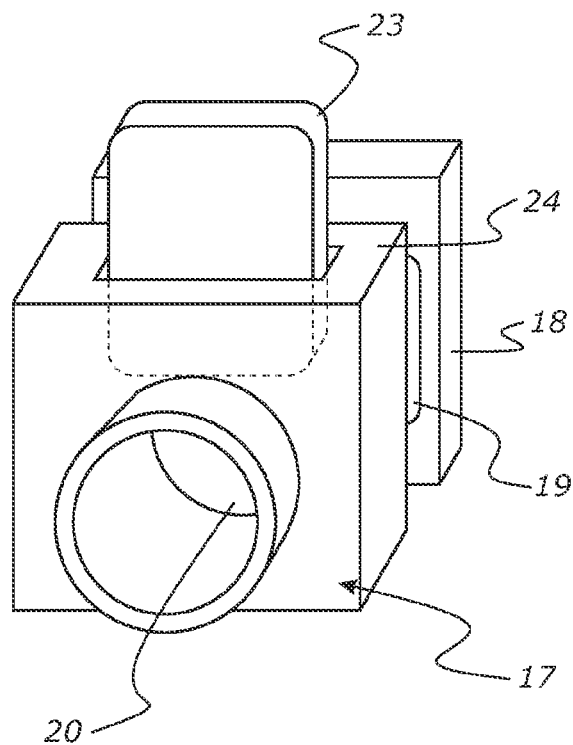
Figure 16B:
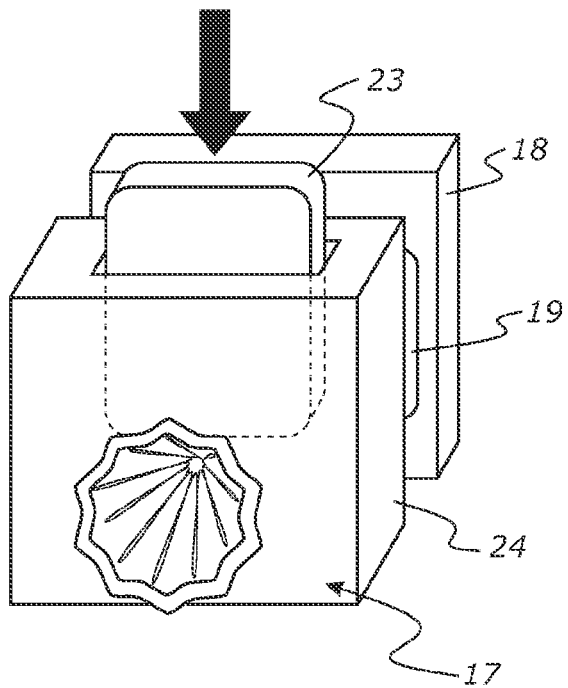

FIGS. 16A and 16B show another embodiment of a user interface which comprises a selectively activated seal.

Figure 17:
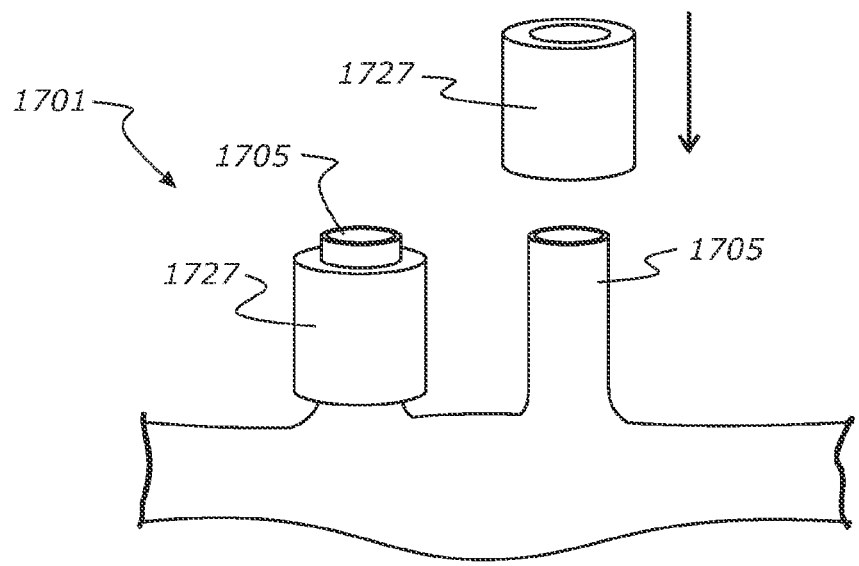

FIG. 17 shows an alternative embodiment for increasing occlusion of the user interface.

Figure 18:
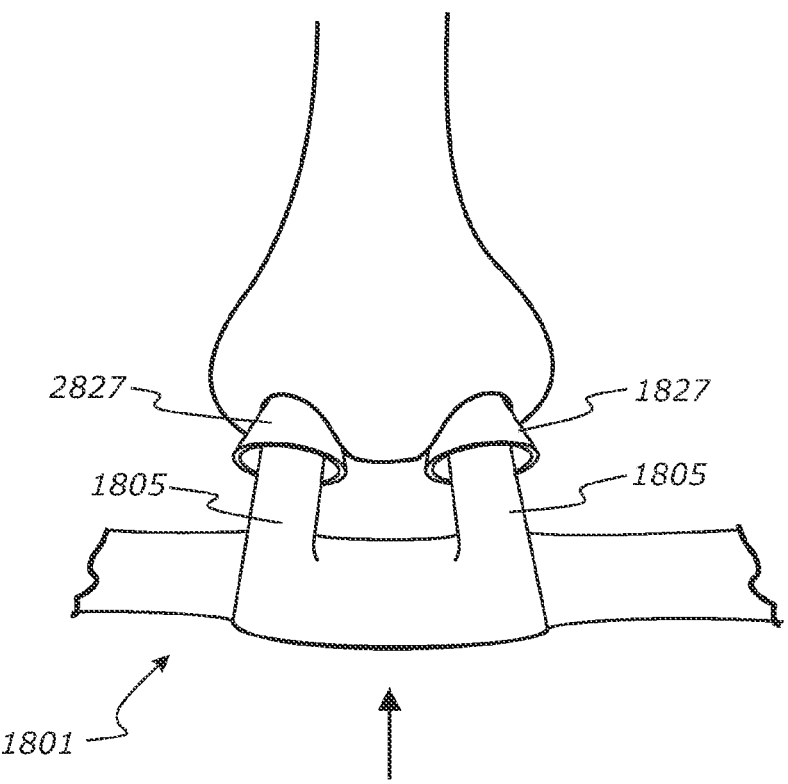

FIGS. 18 and 19 show an alternative embodiment for increasing occlusion of the user interface.

FIG. 20 shows an alternative embodiment for increasing occlusion of the user interface.

FIG. 21 shows an alternative embodiment for increasing occlusion of the user interface.

Figure 22:
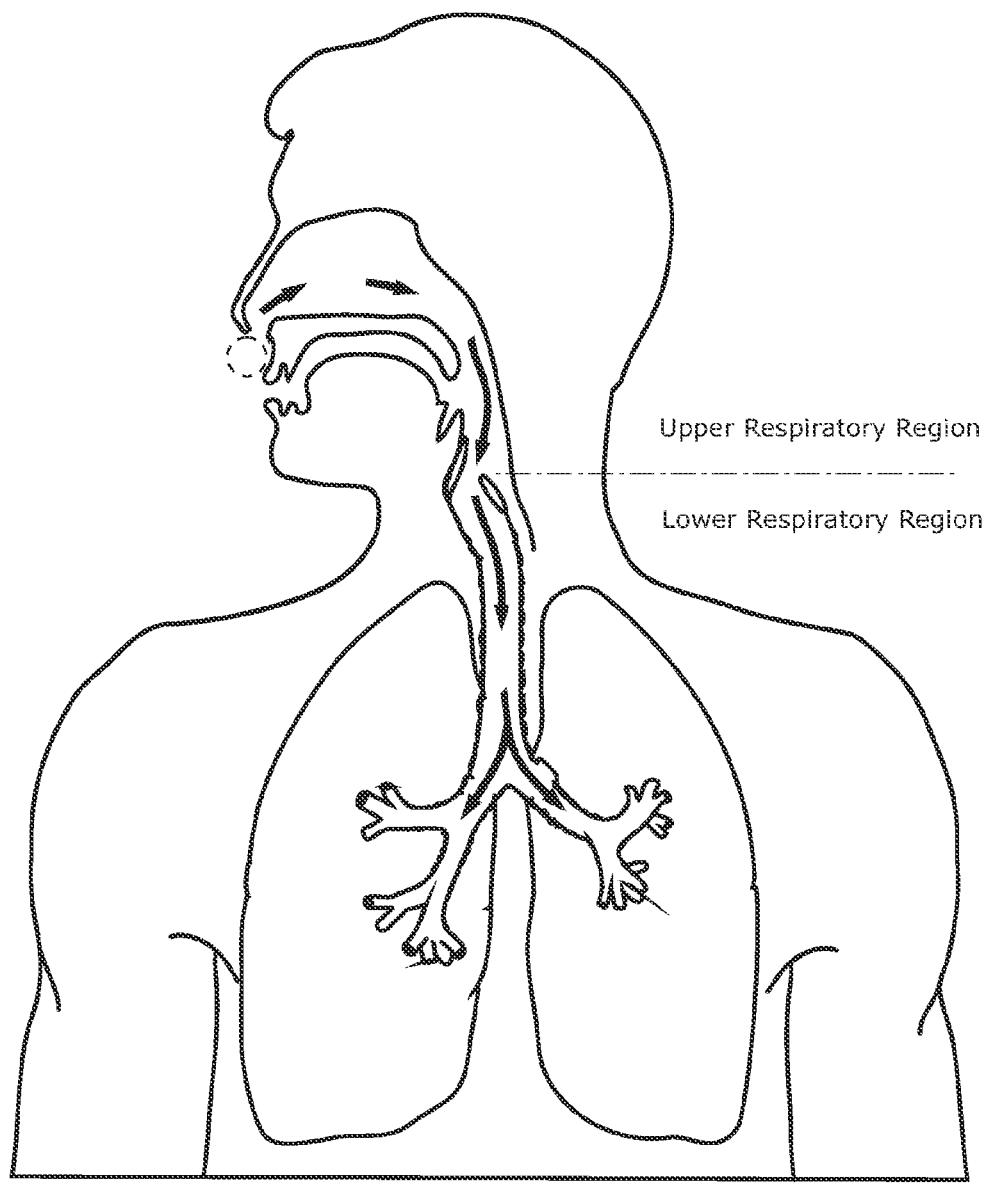

FIG. 22 shows a typical airway of a person, and includes arrows to indicate how a relatively high flow rate of gases supplied to a user may be utilised to effectively push or drive the supplied gases further or deeper into a user's airway than when the person is under normal or typical self-driven respiratory conditions.

DETAILED DESCRIPTION OF THE DRAWINGS

In the field of medical circuits, and in particular breathing circuits for delivering general anaesthetics to users via gases or vapours, maintaining users' physiology at safe levels, namely oxygen, $CO_2$ and anaesthetic drugs is a major concern. Before a user receives anaesthetics via breathable gases, it is critical that a user is provided a sufficient amount of oxygen to flush out the $CO_2$ and the $N_2$ in the user's body during the pre-oxygenation phase, before anaesthetics can be applied.

Atelectasis is the collapse or closure of alveoli in the lungs resulting in reduced or absent gas exchange (ventilation) and occurs in approximately 90% of anaesthetised patients. It occurs both during spontaneous breathing and after muscle paralysis and regardless of whether intravenous or inhalation anaesthetics are used.

The atelectatic lung area can exceed 20%, and in the case of thoracic surgery more than 50% of the lung can collapse.

In addition to atelectasis, airway closure during anaesthesia also causes reduced ventilation and together can account for as much as 74% of impaired arterial oxygenation.

Application of about 10 cmH2O PEEP (positive end expiratory pressure) has been shown to re-open atlectatic lung regions and prevent airway collapse, however, it is thought this is more likely an effect of increased inspiratory and expiratory airway pressures rather than PEEP itself.

The current disclosure is directed to systems and apparatus that provide pressure for example PEEP or inspiration pressure and may at least provide 10cmH2O PEEP to maintain open alveoli.

Atelectasis can remain for several hours after surgery and lung collapse reoccurs rapidly after discontinuation of PEEP.

The provision of a relatively high flow rate of gases to a user or patient can in some configurations be employed to deliver elevated airway pressures during anaesthetic pre-oxygenation, apnoeic oxygenation, and recovery. It will be appreciated that such a therapy of delivery of such a therapy to a user patient may be used in situations other than just during procedures utilising anaesthetics.

As relatively high gas delivery flow rates may be used with the embodiments or configurations described herein, the gases being supplied or delivered to the user or patient can may be delivered to different parts of the user's or a patient's airway.

Such relatively high flowrates of gases may assist in providing the supplied gases into a user's airway, or to different parts of a user's airway, for example such flowrates may allow for a delivery of such gases to the upper, middle or lower airway regions. The embodiments described here provide partial occlusion of the patient's airways, which is advantageous because it prevents atelectasis and prevents alveoli collapse while still providing the benefits of high flow delivery.

A unique ability to maintain elevated airway pressures using such relatively high flowrates in an uninterrupted manner means pre-, during and post-surgery atelectasis and airway closure can be minimised and ventilation (i.e. gas exchange in the lungs) is maintained. For example, in this context "ventilation" does not mean artificial ventilation through a ventilator machine. The embodiments described here provide a modular interface that allows a clinician or user to customize an interface such that therapy delivery can be maintained, or remain substantially uninterrupted even if one airway is in use and cannot have an interface applied to it.

The various disclosed configurations and embodiments herein provide for devices, systems and methods for enhancing an ability to delivery elevated airway pressures and do so without interruption for a user or patient.

Patient interfaces, such as full-face masks (including oro-nasal masks) and nasal cannula or nasal pillows or nasal plugs or nasal masks typically provide for a particular delivery of gases for administration or provision of a desired gas therapy to a user or wearer of the interface.

Clinicians may wish to vary the flow of gas that is delivered to the patient, for example over the breath cycle, to control the variation of the delivered pressure. Currently, flow delivery to the patient can only be controlled at the gas source. Conventional cannula designs are unsealed interfaces that use a flow-based respiratory support. This can make it difficult to control the pressure delivered to the patient.

In some instances, there may be a desire for a user to be provided with multiple therapies or the capability for such therapies which would otherwise be delivered by different patient interfaces.

There are instances in which a clinician may want to increase the pressure delivered to the patient by using an interface that at least partially occludes the airways of the patient. Partial occlusion allows the benefits of $CO_2$ flushing and prevent barotrauma. The partial occlusion may be fixed or variable by the clinician. Other advantages of high flow delivery include oxygen delivery deeper into the patient's airway. A patient's airway may collapse when the patient is anaesthetised.

There are also situations where a clinician will be performing a procedure in which the patient's mouth needs to be open, for example, to insert an instrument, and the high flow therapy and pressure of that therapy needs to be substantially or entirely maintained. The interfaces described herein allow insertion of instruments, into the patient's mouth and/or their nose, without having to remove the interface and/or stop the high flow therapy, and are able to partially occlude, partially seal, or seal around the inserted instruments. The interfaces may self-seal when no instruments are inserted.

Some of the configurations described below relate to a nasal interface and a mask. It will be appreciated that, in-use, the mask is to be placed over the nasal and/or oral area, preferably both the mouth and the nose, of a user for conveying gases to and/or from the user from a gases supply system (not shown) via an aperture or a port provided on the mask. A gas conduit extends into an interior volume of the interface also for supplying gases to and/or from the user from a gases supply system (not shown). In the configurations shown and described below, the interior volume is formed by an interior of the interface and the face of the user, when the interface such as the mask is worn by the user.

In some configurations, the gases supply system which is in gases communication with the gas conduit and the interface via the aperture or the port respectively are separate and independent of each other. In one configuration, the gases supply system which is in gases communication with the aperture or the port of the mask is a part of an anaesthesia system comprises an anaesthesia machine for delivering anaesthetics to the user, whereas the gases supply system which is in gases communication with the gas conduit is a high flow humidified oxygen delivery system. The nasal interface, such as a nasal cannula, may be provided at an end of the gas conduit and within the interior volume of interface for providing for example a high flow of oxygen or blended gases directly into the nares of the user.

The mask comprises a body, such as a shell. The shell may be made of any suitable materials such as polycarbonate, plastic and similar thereof. At or adjacent the rim of the body, there is provided a seal that accommodates the creating or forming of the seal between the interface and the user's face and/or a component so provided on said face. The seal may be integrally formed with the shell such as by injection moulding, or it may be formed as a separate component by any suitable process and then attached to the shell. The seal is preferably made of a soft, flexible material to readily conform to the facial profile of a user when the interface is worn by the user to create a seal between the user's face and the interface. Preferably the seal is a substantially gas tight seal so the user only breathes in and/or out from the conduit or the interior volume or both.

The cannula comprises a body with a pair of prongs that extend in to the nares of the patient. The cannula is or comprises a soft material. The cannula and prongs may be formed entirely from the soft material or may include a relatively rigid portion that is overmoulded or co-moulded with a soft material. The cannula may include headgear such as a bifurcated headgear to retain the cannula on the patient's head.

Patients that may benefit from the user interfaces described herein include patients with OSA (prone to collapsed airways), ARDS (stiff lungs), high BMI or obstetric patients (compression atelectasis due to additional weight on lungs. Reduced FRC), chronic obstructive pulmonary disease (COPD) (stiff lungs), or pneumonia (atelectasis).

Figure 1A:
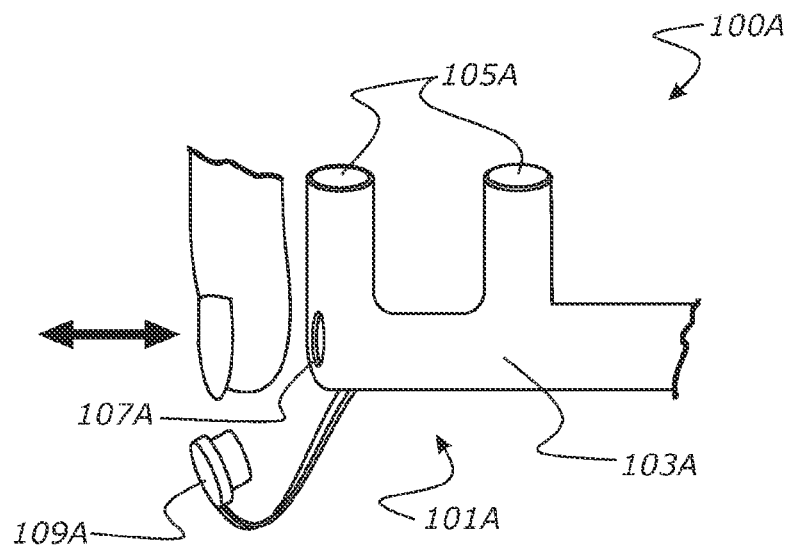
FIGS. 1a and 1b show configurations having manually sealable port on the cannula.

The configuration shown in FIG. 1a allows immediate adjustment of flow delivery. In particular, this configuration allows manual control of high flow gas delivery.

A user interface 100A has a nasal cannula 101A having a body portion 103A locatable upon a face of a patient in an operational position, at least one nasal prong 105A extending from the body portion, the nasal prong being adapted to direct a flow of gas into a nare of the patient's nose when the body portion is in the operational position. In the configuration shown, the user interface has two prongs 105A.

The user interface also has a port 107A located at or near the body 103A portion, and a flow controller, in the form of a plug 109A, for selectively closing the port.

This configuration allows a clinician to watch/monitor a patient or user while affecting pressure to check the patient's response and adjust the flow delivery accordingly. Also, the pressure can be relieved instantly if a risk of barotrauma is detected.

The port 107A and the plug 109A are arranged to allow at least part of the flow of gas to vent to control the flow of gas into the nare of the patient's nose from the nasal prong 105A. The clinician can occlude/seal or remove the occlusion/unseal the port 107A on the cannula 101A, as desired. Sealing or closing the port 107A means full flow is of gas is delivered to the patient or user. Unsealing, removing the occlusion, or opening the port 107A creates pressure relief by allowing the flow to vent, as shown in FIG. 1a. If the clinician wishes deliver the flow for an extended period of time, the port 107A can be sealed with the removable plug. The flow of gases can be varied over the breath cycle (eg: closed during inspiration, opened during expiration to reduce pressure and risk of barotrauma, or vice versa), over a longer period of time (eg: left closed for 5-10 breaths, or 30 seconds of apnoea, as a lung recruitment manoeuvre), or a shorter period (eg: to create high frequency oscillations/oscillatory jet ventilation)

The port 107A may be sized to vent a certain amount of flow (eg: vent 401 pm when run at 701 pm). Other venting volumes are contemplated. In some configurations the volume vented is a percentage or ratio of the total flow.

The port 107A may be made of an expandable material (eg: elastic polymer). When greater flow is delivered, the back pressure in the manifold will be greater so the port will open wider. This may allow the flow to vent a known proportion of the delivered flow (eg: 50%).

Figure 1B:
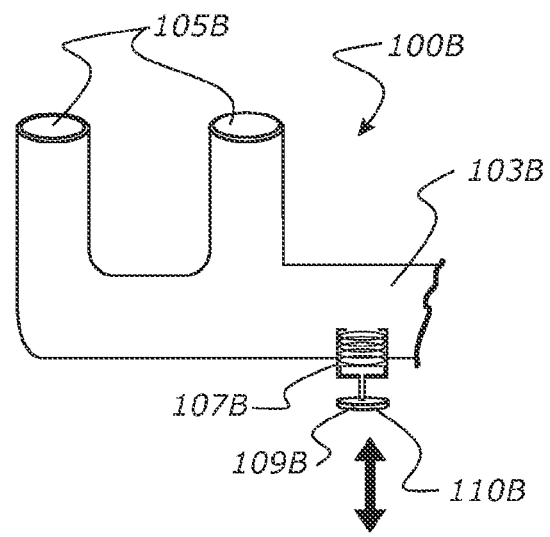

An alternative configuration is shown in FIG. 1b. This configuration is similar to the configuration shown in FIG. 1a and like numbers are used to indicate like parts, except B is used in place of A. In this configuration, the port 107B may comprise a pressure relief valve 109B that can be activated by a depressing a button 110B. Here the valve 109B is naturally closed and pushing the button 110B allows flow to vent through the valve 109B. Alternatively, the opening could have an (adjustable) PEEP valve.

The interface 100A/100B could be used in conjunction with a sealing mouthpiece to prevent mouth leak and create a completely sealed interface.

Figure 2A:
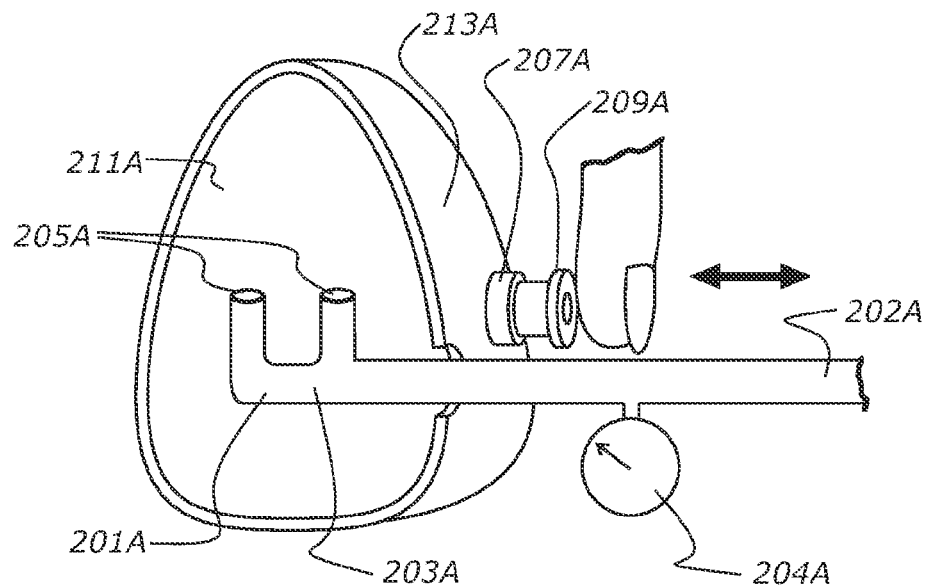
FIGS. 2a and 2b show configurations having a sealable port on the mask.
Figure 2B:
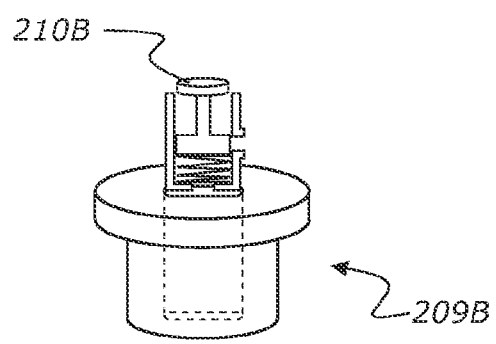

With reference to FIGS. 2a and 2b, another configuration of the user interface is shown. This configuration has an oro-nasal anaesthetic mask 211A placed over the nasal cannula 201A. This configuration has the nasal cannula provided with a cannula gas flow supply and the oro-nasal mask provided with a mask gas flow supply that is able to seal over the nasal cannula, in use. The mask may include a depression in the outer edge or the seal portion of the mask to allow sealing over the supply tube to the nasal cannula.

A flow controller, in the form of a cap 209A, is attached to a port 207A of the mask 211A with an opening through it. The port 207A may be located at or near a body portion 213A of the oro-nasal mask. The port 207A and the cap 209A are arranged to allow at least part of the flow of gas to vent to control the flow of gas into the patient's airway. In particular, an opening on the cap 209A can be occluded or left open to control pressure delivery to patient (FIG. 2a). Sealing the cap 209A creates additional pressure. High flow is not able to vent to atmosphere until the opening is released again. Building/releasing the pressure in the sealed interface allows manual breaths to be simulated with high flow (where releasing allows expiration). Building pressure in the patient's airways prevents or at least substantially inhibits the patient's airways from collapsing. This could be useful in apnoeic periods for lung recruitment or to stimulate spontaneous breathing.

Alternatively, the flow controller could be a pressure relief valve 209B that can be activated by a depressing a button 210B(See FIG. 2b). In this alternative, the valve 209B is naturally closed and pushing the button 210B allows flow to vent through the valve 209B. Alternatively, this could be an (adjustable) PEEP valve.

The mask 211A may have a self-sealing valve when the cap 209A/210B is removed, so that if the clinician wishes to maintain pressure for a long period of time, they can just remove the cap. The high flow gas supply may have a pressure relief valve to prevent hyper-inflation.

Alternatively, the mask could be connected up to a gas conduit and the cap inserted at the end of the conduit; that is, instead of a reservoir bag. If the cap is removed and replaced with a bag, this allows the user to revert to normal bag-ventilation.

There may be a pressure gauge 204A on/near the cannula or mask for visual feedback to the user. If the mask is connected to the anaesthetic machine the pressure reading from the mask may be read off the gauge there instead.

Methods of flow variation and port sizing described in relation to the previous configuration also apply.

Advantages of this configuration include:

Sealed interface allows better pressure control

Immediate adjustment of flow delivery and/or pressure delivery (programming a flow variation cycle in software/on the device takes time and cannot be implemented instantly. Also any minor adjustments require re-programming).

Can watch/monitor patient while adjusting pressure to respond accordingly.

Measurement of delivered pressure within sealed interface.

Sometimes a clinician may wish to deliver respiratory support through a nasal interface, such as during intubation attempts, sometimes they may wish to deliver respiratory support orally as the patient is a mouth breather, or the clinicians wants to insert instruments through the nose. Sometimes it may be desirable to seal the interface to create more pressure, or have greater control over the delivered patient breath, however sometimes it may be desirable for the interface to be non-sealing to enable pressure release.

Figure 3A:
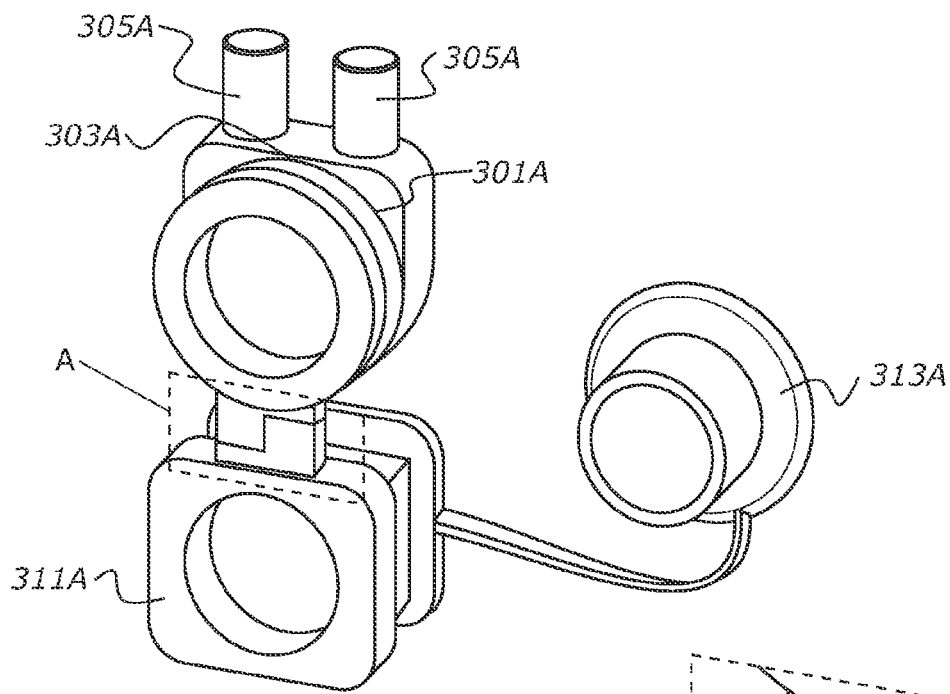
FIGS. 3a to 3d show another configuration, in the form of a modular, adaptable interface that has two parts: a nasal cannula and a mouth insert.
Figure 3A:
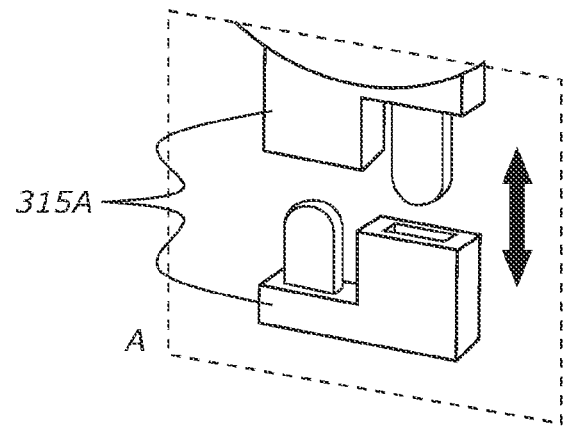

With reference to FIG. 3a, another configuration of the user interface is shown. In this configuration, the interface is a modular, adaptable interface that has two parts: a nasal cannula and a mouth insert. The parts can be attached together (eg: using mechanism as shown in FIG. 3A) or used separately, as desired. In a further alternative, they may be permanently attached together. A gas supply conduit can be inserted into either part. An opening for the gas conduit may be a standard taper connection to permit connection of most gas supply tubes. The gas may be delivered though whichever interface the gas supply conduit is inserted into, or the interfaces may be fluidly connected and the gas is delivered through both interfaces. The mechanism 315A may be self-sealing such that gas does not leak out when the parts are disconnected.

The mouthpiece 311A may be blocked with a plug 313A to maintain the pressure and prevent leak of nasally delivered high flow for mouth-breathers, and prevent leak of delivered high flow through the mouth. The plug 313A may contain a valve (eg: duckbill as shown in the centre of the illustrated cap) to allow instruments to inserted while maintaining a seal. A duckbill valve creates a seal around the instruments that may be inserted into the patient's mouth. After the instrument is removed, the duckbill valve closes and maintains the seal.

Figure 3B:
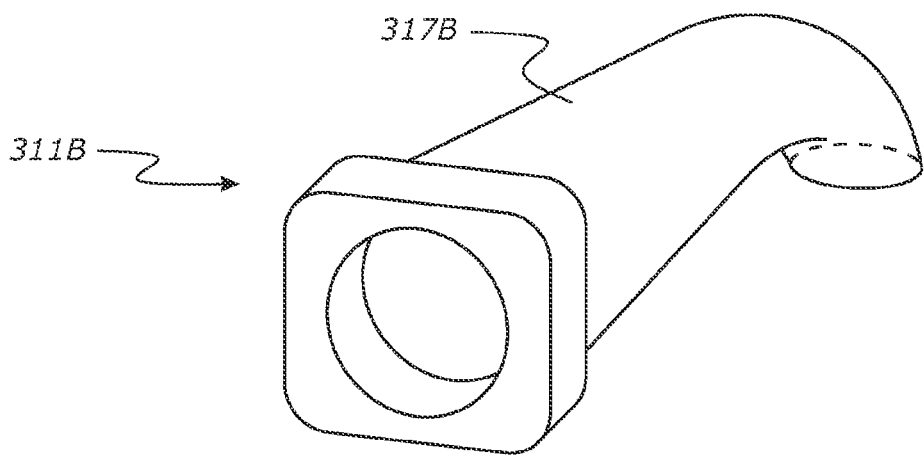
Figure 3C:
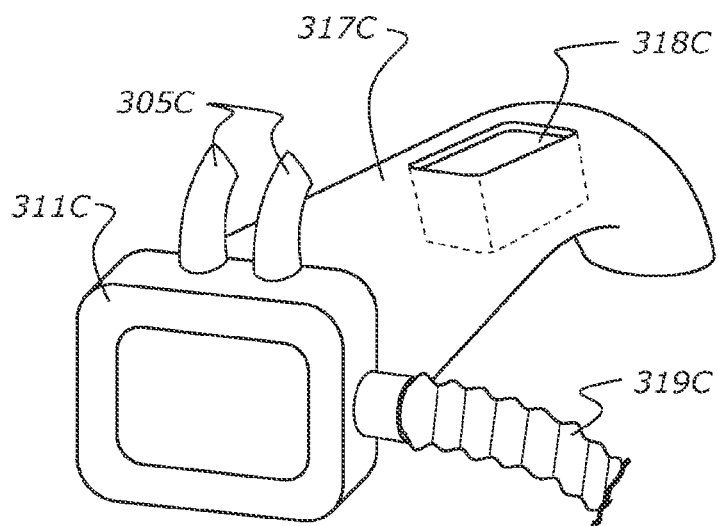
Figure 3D:
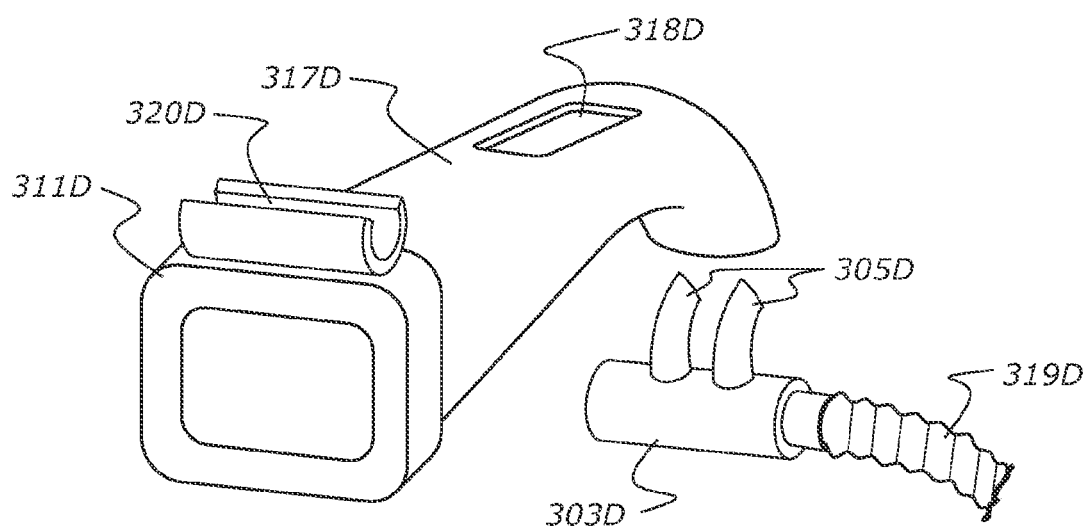

FIG. 3b shows an alternative mouthpiece 311B that may have an extended section 317B into the airway. FIG. 3c shows another alternative mouthpiece 311C with an extended section 317C into the airway. FIG. 3d shows a further alternative mouthpiece 311D with an extended section 317D into the airway. The extended section 317B/317C/317D could be curved, to lie over top of the tongue, which may be more comfortable for the patient. The extended section 317D has an opening 318 that may also act as an opening to insert instruments through the nasal passages into the airways. The shape may also help guide instruments down the airway, and the extension may help promote $CO_2$ flushing and $O_2$ delivery deeper into the airway. A patient's airway may collapse when the patient is anaesthetised. The extended section 317B/317C/317D helps to maintain the patient's airway open and promote gas exchange in the case of potential collapse. In this embodiment, there is an opening at the back of the extended section to allow gas flow from the nasal passages into the lower airways. The opening allows high flow to be delivered into the lower airways and lungs, which may not occur in some situations if high flow is delivered to nasal cavity alone. The mouthpiece may also have nasal prongs attached which may deliver high flow. The prongs may be permanently attached to the mouthpiece (as shown in FIG. 3C) or the mouthpiece may have an attachment system, such as a clip 319D or groove (as shown in FIG. 3D), that a nasal cannula may be attached to or inserted into.

Figure 4A:
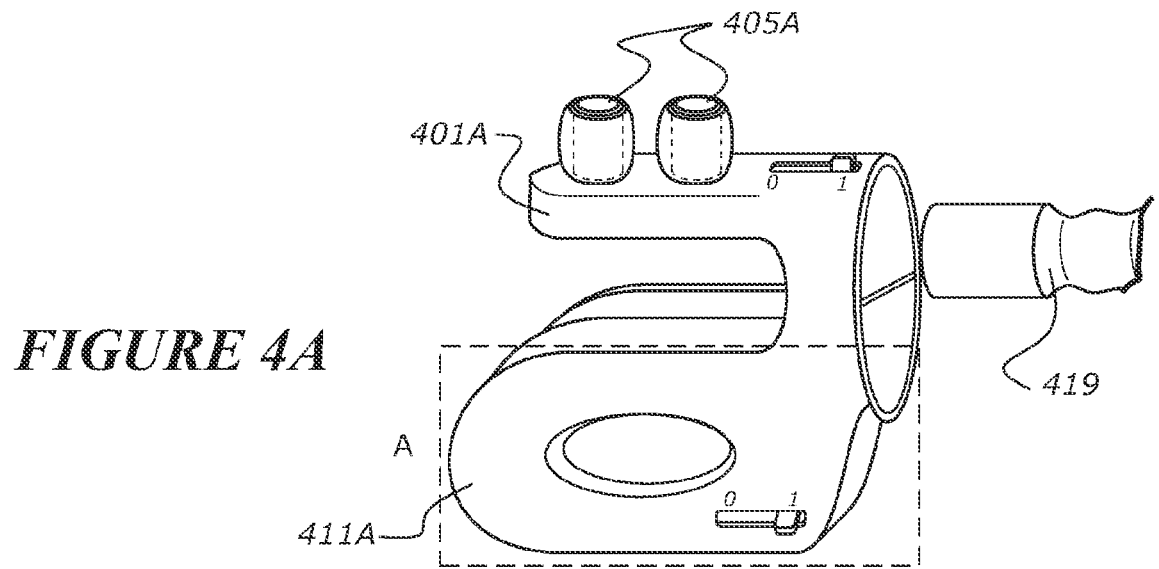
FIGS. 4a to 4f show another configuration, in the form of a modular, adaptable interface that has two parts: a nasal cannula and a mouth insert.
Figure 4B:
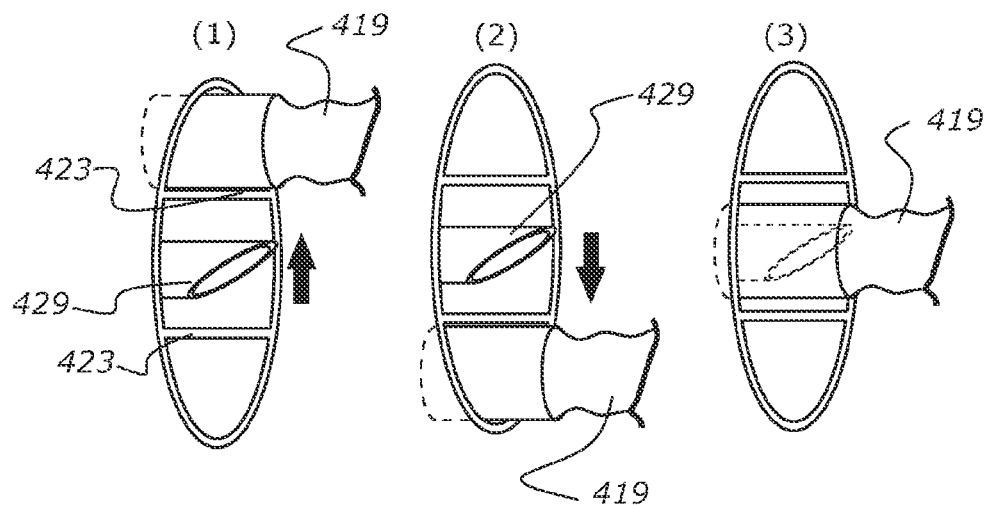

With reference to FIG. 4a, another configuration of the user interface is shown. In this configuration, the user interface has two parts, a nasal cannula 401A and a mouth insert 411. This embodiment is a modular interface that allows a clinician or user to customize an interface such that therapy delivery can be maintained, or remain substantially uninterrupted even if one airway is in use and cannot have an interface applied to it. The parts can be attached together (eg: using mechanism 315A in FIG. 3A) or used separately, as desired. Alternatively, they may be permanently attached together. The gas supply conduit 419 may be inserted into either part. If the parts are attached together, the gas will be delivered though whichever interface the gas supply conduit 419 is aligned with. The gas supply conduit 419 may be moved up and down within the combined interface to realign the gas entry point. For example see FIG. 4b: if the conduit 419 is pushed to the uppermost position (1) (aligned with cannula), gas will be delivered through the prongs 405A. A valve will seal the flow from entering the mouthpiece. The valve may be a flap 429 that can open/close as the conduit 419 pushes past. There may be rails 423 on the wall of interface opening to position/lock the conduit 419 into place. If the conduit 419 is pushed to the lowermost position (2) (aligned with mouth), gas will be delivered through mouth insert. If the conduit 419 is in the middle the valve is pushed open allowing flow to be delivered to both the patient's nose and mouth.

Alternatively, it may be possible to connect more than one gas supply to the interface, (eg: high flow through unsealed nasal prongs plus additional pressure support through sealed oral part, or high frequency oscillations though one part, with base flow/pressure through other). The high flow therapy may be delivered through the nasal prongs plus gases supply may be delivered through the oral part. Alternatively, high frequency oscillations may be delivered through one part, with a base flow or pressure through another part. In another alternative, high flow may be delivered through the nasal prongs and the gas supply may be delivered through the sealed oral part.

Figure 4C:
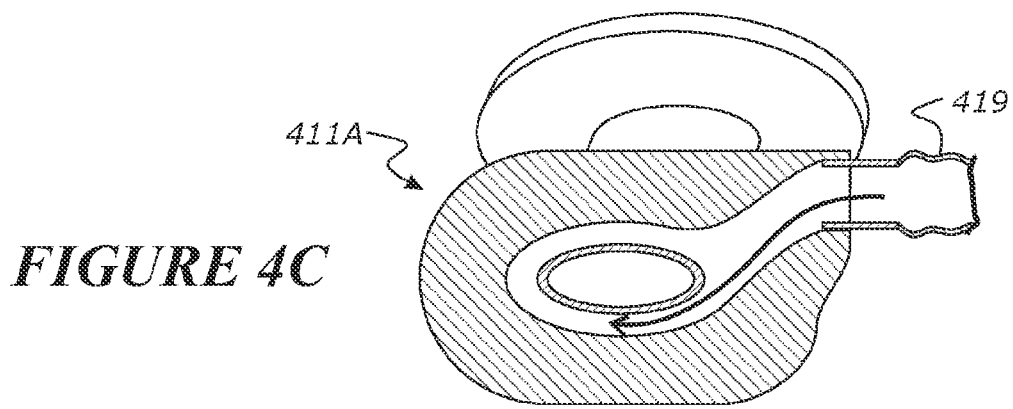

FIG. 4c shows a cross-section through a plane of the mouth insert 411, with a possible flow path to the mouth: flow comes from the gas conduit 419 on the right hand side into the lower part of the interface. The flow passes into the mouth co-axial to portion extending into the user's mouth. A co-axial flow ensures even flow distribution into the user's mouth (as opposed to flow being delivered down a channel on one side of the insert, into one side of the mouth)

Figure 4D:
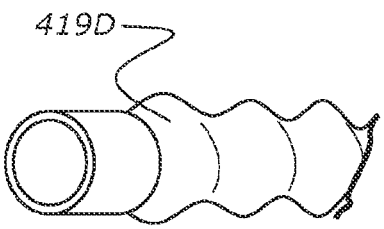
Figure 4D:
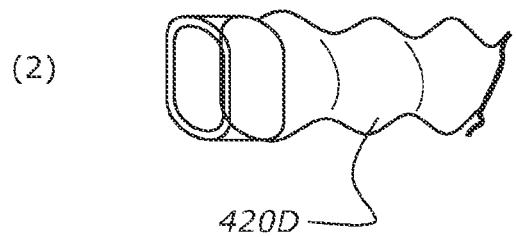

The interface could allow connection with a standard gas conduit 419D (eg: FIG. 4d (1) or may use a specialised conduit connector 420d that engages with the interface more securely (eg: FIG. 4d (2)). FIG. 4d(2) shows a conduit connector that is flat or has two flat sides to facilitate sliding up and down within the interface and the top of the conduit connector being curved with the top of the openings in the interface, and the bottom may also be curved to correspond to the shape of the bottom of the connector to create a seal.

Figure 4E:
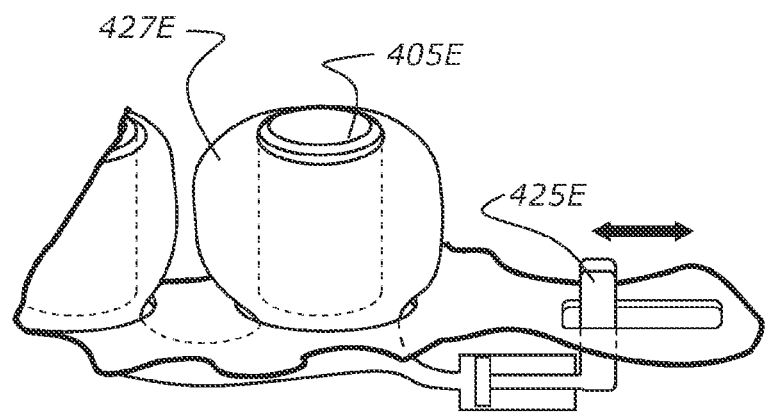

The interface can be optionally partially occluded, partially sealed, or sealed, easily and immediately. FIG. 4e shows one example. The nasal prongs can be inflated to create a seal or at least a partial seal with the one or more nostrils or nasal openings of the patient. The nasal prong may be pre-inflated and deflated by a user or clinician or may be initially deflated and inflated by a user or clinician. Preferably there is a partial seal in which at least above 70% of the nasal openings are sealed to create pressure but also maintain the advantages of high flow therapy.

In some instances, the interface being sealed may be important for patients with weak airways or obese patients. The mouthpiece being sealed provides a seal in the patient's airways or at least a partial seal with the airways of the patient.

In other instances, the interface may not be completely sealed because that may cause risk of barotrauma due to excessive pressure in the airways and the interface would not then provide the benefits of flushing.

Figure 4F:
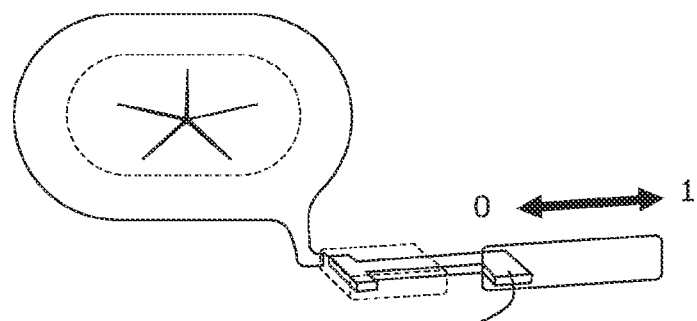

The prongs may be inflated, creating an occlusion, partial seal, or seal in the user's nares, when a lever 425E is pushed to the left, which pushes the gas from the syringe into inflatable cuffs 427E. The partial seal may be fixed or variable by the clinician. The nasal prong may be pre-inflated and deflated by a user or clinician or may be initially deflated and inflated by a user or clinician. There could be two controls to seal each prong 405E independently (eg: to leave one less sealed for insertion of nasal instruments). FIG. 4f shows a similar arrangement for the mouthpiece where moving the lever 425F to the left inflates the seal, occluding or closing off the mouth. Moving levers to the right draws air from the cuffs to deflate them. In this arrangement the cuffs are connected for simultaneous seal formation on both nostrils, i.e. the cuffs are simultaneously inflated. It is possible to selectively seal/partially occlude either the patient's nose or mouth. Alternatively it is possible to selectively seal/partially occlude both of the patient's nose and mouth. In a further alternative, it is possible to selectively seal/partially occlude either the patient's nostril or mouth and nostril in combination.

It may still be possible to insert instruments through/past the seals. Eg: a video-guided bronchoscope may be used through the centre of the inflated mouth seal where limited direct visualisation of the airway is required. This enables respiratory support and delivered pressure to be maintained throughout the procedure and as the interface can hold a partial occlusion, partial seal, or complete seal around the scope. The partial occlusion may be fixed or variable by the clinician. The continued delivered pressure can help also to keep the airways patent.

Figure 5A:
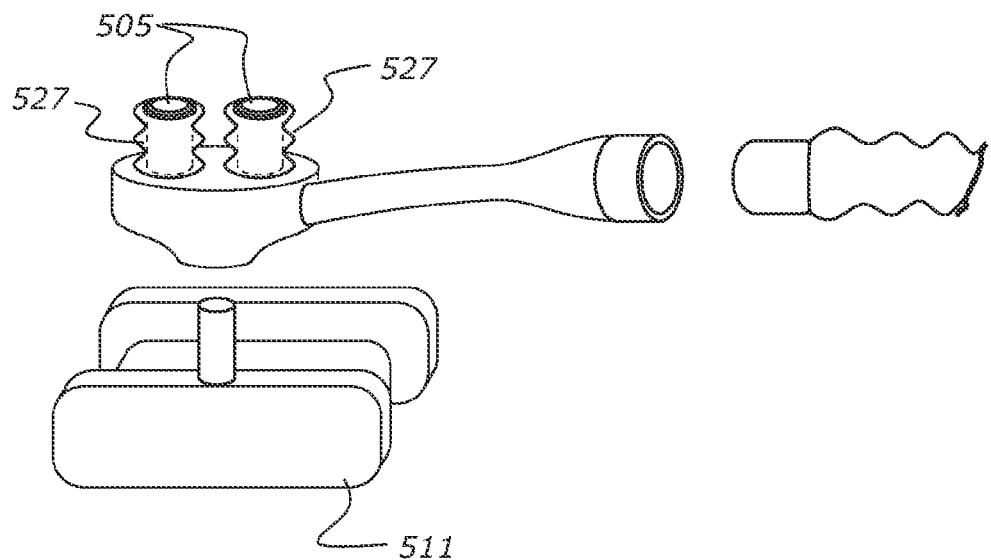
FIGS. 5a and 5b show another configuration, in the form of a modular, adaptable interface that has two parts: a nasal cannula and a mouth insert.
Figure 5B:
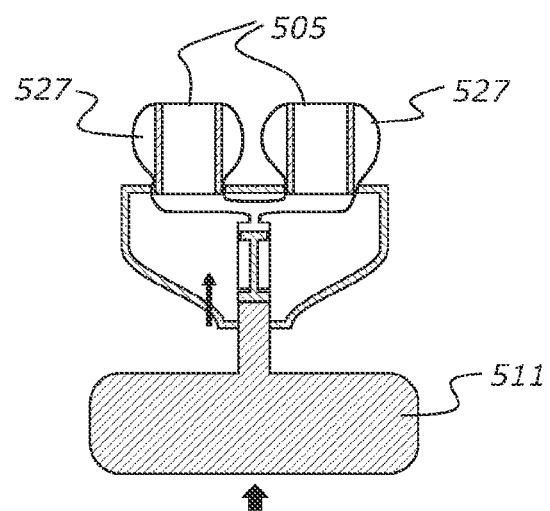

As an alternative, the addition of part of the interface could create or remove a seal. See FIGS. 5a and 5b. Flow is only delivered to the prongs 505. It is assumed that if a mouthpiece is desired, it is to prevent leak and increase the delivered pressure. Therefore, it may be desirable to also seal the prongs 505. Here the insertion of the mouthpiece simultaneously inflates the cuffs 527 by activating the integrated syringe to push air into the prong cuffs. The cuffs 527 may be pre-inflated and deflated by a user or clinician or may be deflated and inflated by a user or clinician.

Where prong cuffs are inflated, they may act to reduce leak from the airway, partially or fully seal. It may be most beneficial to reduce leak so that with a large gas flow to the patient a higher pressure is achieved but maintaining a large leak flow between the prongs and the nares. This may be useful to maximise the effects of $CO_2$ flushing achieved with high flow and to allow expiration and prevent barotrauma. Prong cuffs may be inflated and deflated from a distance away from the patient via a small diameter conduit that transfers the air to the cuffs.

The gas supply may contain a pressure relief valve to prevent hyper-inflation (eg: in the case of a continuous flow delivery and a fully sealing interface).

An interface, such as a nasal cannula, may be modified or designed so as to allow for improved or greater ease of insertion or application of instruments into the patient's airway. This alternative is described below in relation to the embodiment shown in FIG. 21.

The high flow gases, such as air or air/oxygen mixture or high flow oxygen, can be selectively delivered into the patient's nares via nasal prongs or into the mouth via a mouth piece. Alternatively, the gases can be delivered to both patient's nares and mouth with minimal occlusion for high flow delivery. The clinician can also selectively apply a partial occlusion or complete occlusion/seal to either airway. The partial occlusion may be fixed or variable by the clinician.

With reference to the embodiments of FIGS. 4a to Sb, the interfaces may partially occlude, partially seal, or completely seal the patient's nares or mouth.

The mouthpiece of FIGS. 4A-SB could also have extended section as in FIG. 3b or 3c or 3d.

The interfaces shown and described in relation to FIGS. 3A, 4A-SB are modular and customisable. The interfaces described allow a clinician to selectably seal the patient's nose or mouth using one of the interfaces. The clinician may selectively create a seal or partial seal/occlusion in the patient's nostrils, mouth or create a partial seal/occlusion in both.

Figure 6A:
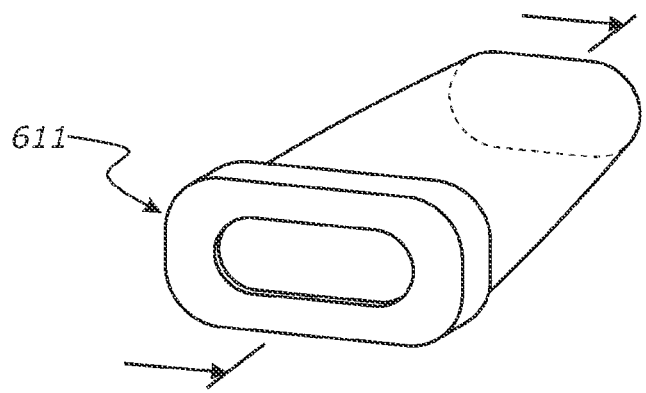
FIGS. 6a to 6c shows another configuration, having breath-controlled sealing between the nasal cannula and the mouth insert.
Figure 6B:
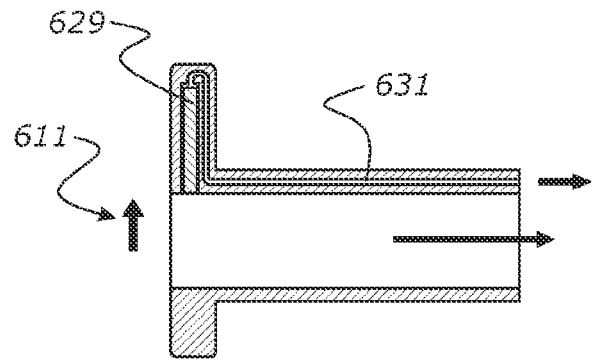
Figure 6C:
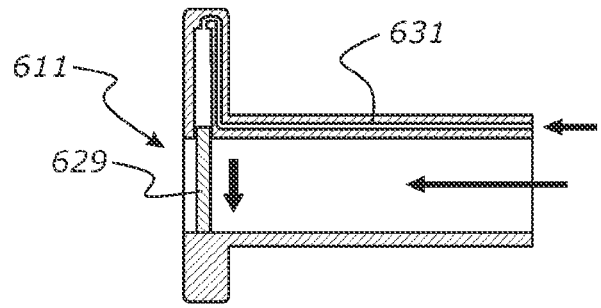

With reference to FIGS. 6a to 6c, another configuration of the user interface is shown. This configuration is a modification or alternative to the configurations shown and described in relation to FIGS. 4a to 4f and FIGS. 5a and 5b. An advantage of this configuration is that it requires no intervention from the user or clinician to create/release or release an occlusion or seal.

FIG. 6a shows a mouth insert 611a that can be used to control pressure support (could be used with nasal cannula, eg: could be used in one of the configurations described above). The mouth insert opens/closes or partially closes with patient's inspiration/expiration, eg: opening or closing could be controlled by a valve triggered by negative inspiratory pressure.

For example see FIG. 6b: a pressure line 631 runs from the right hand side of the mouthpiece (into patient's airway) to above a cavity that contains a cover slip 629. When patient inspires a negative pressure is generated in the pressure line 631, creating a small vacuum in the cavity and holding the cover slip 629 up, so the mouthpiece 611 is open allowing air to flow to the patient. When patient expires, the pressure is positive forcing the cover down, closing off mouthpiece.

This could be useful if the clinician wants to reduce the inspiratory resistance to flow, or promote $CO_2$ flushing by allowing the nasal flow to pass out of the mouth during inspiration, and also wants to provide increased pressure during expiration, or PEEP to maintain open alveoli in the lungs to aide in lung recruitment, and/or to prevent airways from collapsing.

In the opposite case, the cover 629 may be closed during inspiration, and open on expiration. This could be useful if the clinician wants to limit inspiratory entrainment through the mouth (ie: have flow only delivered through nasal cannula), to prevent entrainment dilution of nasally delivered flow. However they may wish to release pressure on expiration if there is a risk of barotrauma (pressure is higher on expiration with high flow because of the opposing flows between the delivered flow and the patient's expired breath.)

Advantages of these configurations shown and described in relation to FIGS. 4a to 4f, FIGS. 5a and 5b, and FIGS. 6a to 6c include:

Interface is modular and customisable.
Allows partial or complete sealing of the airways and therefore increased pressure delivery compared with normal unsealed nasal cannula, but design may be less claustrophobic to patient than a face mask, improving tolerance and therefore the ability to delivery therapy continuously.
Allows insertion of instruments, into mouth and/or nose, without having to remove interface.
Allows insertion of instruments while still being able to maintain respiratory support
Can deliver more than one respiratory support simultaneously.
Unrequired parts of interface can be removed, reducing bulk on the face and improving patient comfort.
Design may be less claustrophobic to patient than a mask, improving tolerance and therefore the ability to deliver the therapy continuously/effectively.
Design allows insertion of oral/nasal instruments without having to remove interface.
Design allows option to insert oral/nasal instruments while retaining interface occlusion/seal.
Delivered pressure can be easily and immediately increased or decreased, either completely or variably.
Mouth insert can hold mouth open for instrument insertion or in a particular shape for 'blind'/visually guided intubations or insertion of other airway devices such as bougies.
The mouth insert may be made of a rigid material to help keep the mouth open, allowing instruments to be inserted, better visualisation of airway and preventing patient's biting on instruments, damaging them.
When occluded/sealed and used with nasal high flow, the mouth insert prevents pressure loss from an open mouth, and ensures accurate oxygen/drug delivery by preventing entrainment through the mouth.
Selective sealing by selective inflating or deflating.

It may be desirable to independently, or dependently control the delivered flow/pressure through a mask and cannula used together. This may be useful in cases when anaesthetists want to be able to ventilate via a high flow nasal cannula but may also be more familiar with using a mask. Ventilation is possible due to the pressure that can be created by using the interfaces described while still gaining the benefits of high flow therapy delivery.

The user may wish to have better control over the delivered pressure and/or the amount of $CO_2$ flushing. In addition, hypercapnia can be a concern, particularly during apnoea.

A proposed solution is to provide independent and dependent control of mask and cannula delivered flows.

Figure 7A:
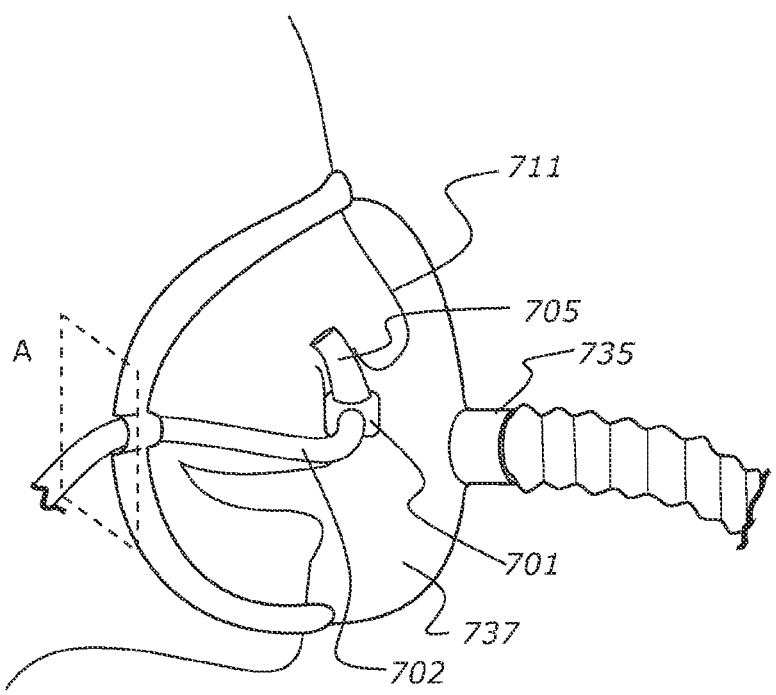
FIGS. 7a to 7c shows another configuration, in which a mask and cannula are used together.
Figure 7B:
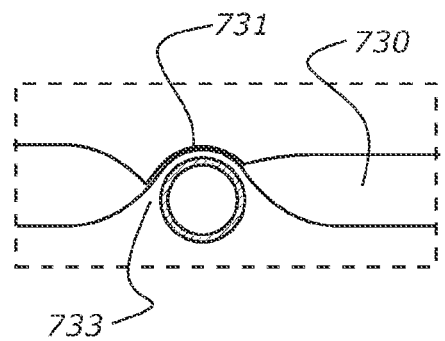

With reference to FIG. 7, another configuration of the user interface is shown. This configuration has a mask 711 applied over the nasal cannula 701 and prongs 705. The mask seal 730 may have a compressed section 731 that can easily mould over the cannula tube, eg: FIG. 7b shows a cross-section through the seal. The mask 711 may clip onto the cannula 701.

According to the disclosure, the interface is configured and adapted to allow intrusion of the gas conduit 702 into the interior volume of the mask 711, while maintaining the substantially gas tight seal between the mask and the user's face and/or the spacer component provided on the user's face.

The mask 711 comprises one or more accommodation sites or portions 733 adapted to facilitate intrusion of the gas conduit into the interior volume of the body while maintaining the seal between the interface and the user's face. The one or more accommodation sites or portions 733 is provided on or adjacent the seal and/or the body. In the embodiment shown, the accommodation site is provided as a cut-out in the seal. The cut-out has a profile which is similar, or slightly smaller in dimension than the cross-section of the gas conduit. This is so that the gas conduit can extend into or out of the interior volume of the body without leaving a gap between the seal and the user's face which will then compromise the seal between the seal and the user's face.

The accommodation sites or portions of the interface may allow for the interface to be used with a nasal cannula.

he nasal cannula 701 is used to deliver a relatively high flow of oxygen or a high flow of blended gases or high flow of air. The mask may be used for various other respiratory support or for anaesthetics delivery. As mentioned above, the mask comprises a seal to seal against the user's face when in-use.

The accommodation sites or portions 733 allow for the nasal cannula to be used with the interface without compromising or substantially affecting or interfering with the seal between the interface and the user's face. This may allow for a nasal cannula 701 which for example delivers high flow therapy to be used in combination with the mask 711 which is used to provide other respiratory support. A medical practitioner can adjust or choose which respiratory support to be used on the user without irritating the user by constantly adding or removing the user interfaces, such as the mask and the nasal cannula.

In some other configurations, the accommodation sites or portions allows the interface to be put on a user without first removing the nasal cannula from the user's face. Various sealing structures may be utilised to facilitate a greater ease of switching between respiratory support modes without the need to change or remove one, some or any or all patient interfaces.

Figure 7C:
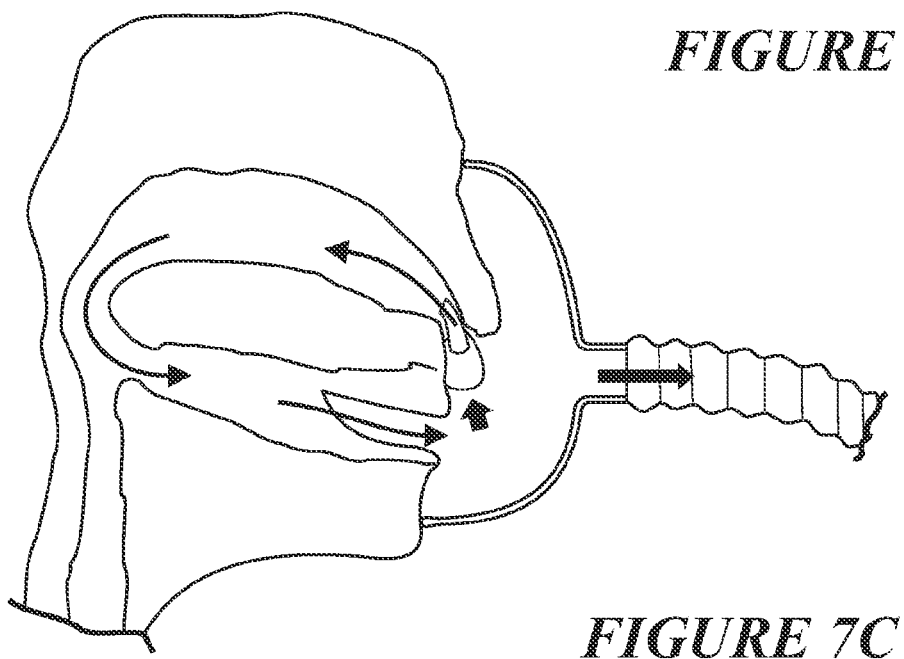

The accommodation site or portions may be provided directly in the seal and/or the body of the mask such as that shown in FIGS. 7a to 7c. In another embodiment, the accommodation sites or portions may be provided as an extension portion of the seal and a cut-out is formed in the extension portion instead of directly in the seal.

A method of providing respiratory support to a patient will now be described. A nasal cannula 701 is placed upon a face of a user in an operational position, the nasal cannula having a body portion and at least one nasal prong extending from the body portion.

Next, a mask 711 is placed upon the face of the user. The oro-nasal mask has a body. The body comprises an aperture or a port 735 allowing for communication of gases to and/or from a gas supply or source to an interior volume of the interface. The interior volume 737 is defined by an interior of the body and the face of the user when in-use, a seal provided for creating or forming of a seal between the user interface and the user's face and/or a spacer component (not illustrated) provided on the user's face. It will be appreciated that accommodation sites will not be necessary if a spacer component is used because the spacer can be appropriately shaped.

A seal is created or formed between the mask and the user's face and/or the spacer component (not illustrated) so provided on said face.

A flow of gas is directed into the user's airway via the nasal prong and/or the oro-nasal mask.

The following cases of mask and cannula delivered flows are possible:

Case 1: High flow may be delivered though the cannula and mask simultaneously, from one or different gas sources. This could be used for mouth breathers to ensure high flow is delivered effectively (preventing mouth entrainment of room air)

Case 2: FIG. 7c. Positive flow delivered through mouth, mask flow is negative (suction). This may help promote $CO_2$ flushing in the airway. Especially if the mouth is open—this could encourage flow circulation in back of pharynx. The narrowing of the airway at the back of the mouth may act as a venturi, entraining even more flow from the cannula than the patient may naturally inspire, and further promoting flushing. If the patient is apnoeic (and not naturally inspiring) this flushing would also be beneficial.

Case 3: reverse of case 2. May be more comfortable for some patients (eg: mouth breathers)

Case 4: reverse of case 2 but high flow is delivered through mouthpiece, or tube inserted in mouth Case 5: flow is varied between case 2 and case 3 (eg: once every breath cycle). This may create greater turbulence in the airway, promoting gas mixing, and further promoting $CO_2$ flushing, or at a higher frequency (eg: 100 Hz)

Case 6: High frequency oscillations though one interface, with a base flow/pressure through the other. Again to help promote gas mixing, while maintaining a base level of respiratory support.

It will be appreciated the above cases are non-limiting examples and the delivered flows may be provided by alternative interfaces or systems.

Conventional high flow interfaces are currently designed only for delivery of gas to a user through the user's nose. In procedures such as endoscopies (eg: bronchoscopies) in can be desirable to provide respiratory support through the mouth so the nose can be accessed. To achieve this, clinicians may put the nasal cannula in the patient's mouth. This can fall out easily, especially if the patient is sedated and it is not comfortable. The clinician may not notice the prongs have fallen out and this can lead to ineffective therapy support and patient deterioration.

With reference to FIGS. 8a to 8h, various configurations will now be described. Each of the following configurations allows the user interface to be convertible between a nasal cannula configuration and an oral gases delivery interface configuration. In the nasal configuration, the user interface comprises a cannula having a body portion, at least one prong extending from the body portion, the prong being adapted to direct a flow of gas into a nare of a user's nose. In the oral gases delivery interface configuration, the user interface comprises a cannula having a body portion, at least one prong extending from the body portion, the prong being adapted to direct a flow of gas into a nare of a user's mouth, and a mouthpiece adapted to surround the at least one prong of the cannula and an outer periphery that substantially conforms to the area of a user's mouth. The mouth piece allows the cannula to be configured to comfortably fit in the user's mouth.

Figure 8A:
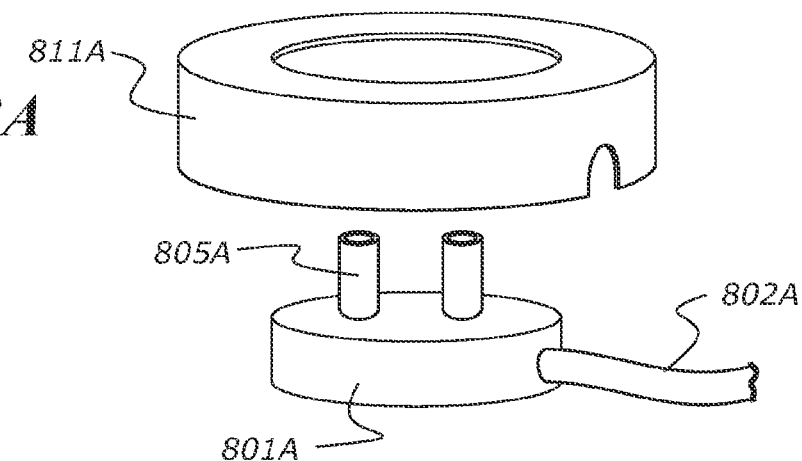
FIGS. 8a to 8h, show configurations that allow the user interface to be convertible between a nasal cannula configuration and an oral configuration.
Figure 8B:
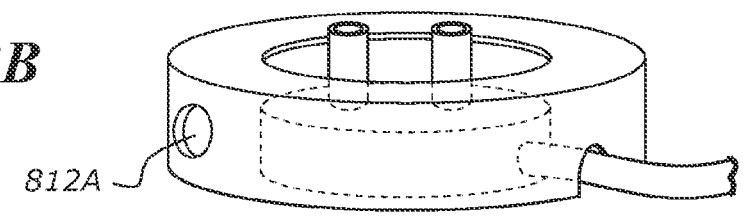

With reference to FIGS. 8a and 8b, another configuration of the user interface is shown. In this configuration, an insert 811A clips over the cannula 801A. The insert 811A is advantageously shaped to the user's mouth. This configuration allows flow from the prongs 808A to be directed into the user's mouth. This embodiment may contain an opening 812A on the mouthpiece to allow venting/exhalation when in the user's mouth. The clip-over section may be bought as separate part. The cannula can be left as normal until adaption is required. The flow of gas is provided to the interface by a gases conduit 802A.

Figure 8C:
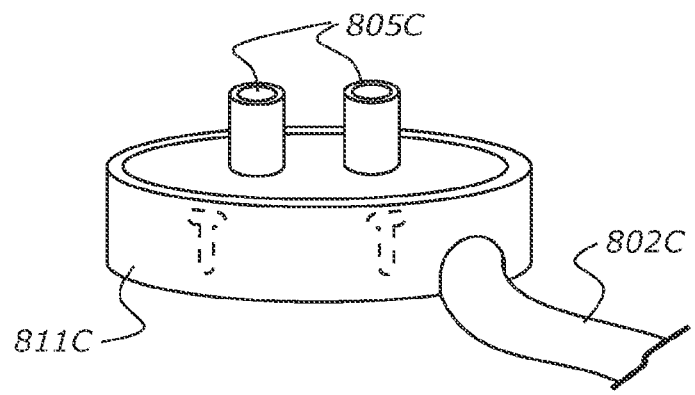
Figure 8D:
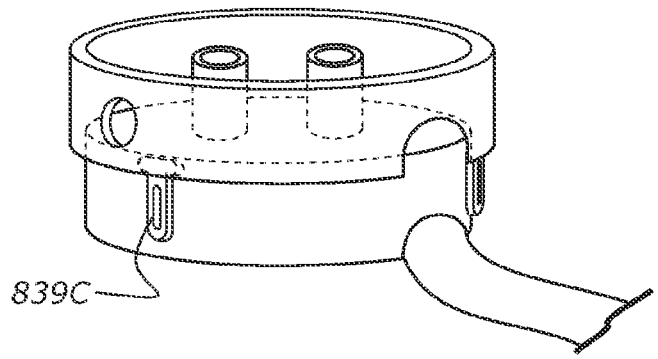

With reference to FIGS. 8c and 8d, another configuration of the user interface is shown. This configuration has a mouth piece 811C that slides up the main cannula body on rails 839C. The user interface has stops on the rails to prevent the mouthpiece completely sliding off, which also prevents the mouthpiece 811C being lost. In this configuration, the tube 802C can sit well outside mouth. The mouthpieces described herein can be shaped to fit into the patient's mouth and create a complete or at least substantial seal with the mouth. The mouthpieces of FIGS. 8a-8d are soft so as to sit comfortably in the mouth and/or seal in the mouth.

Figure 8E:
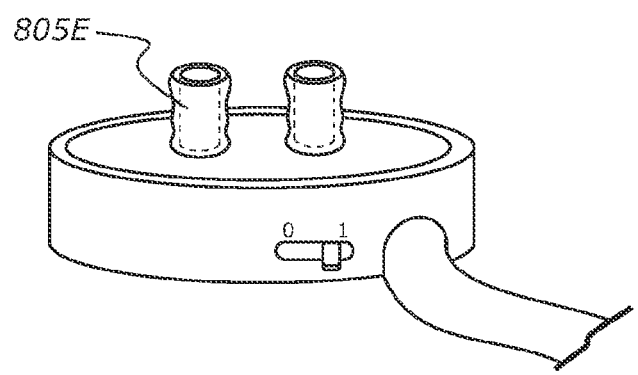
Figure 8F:
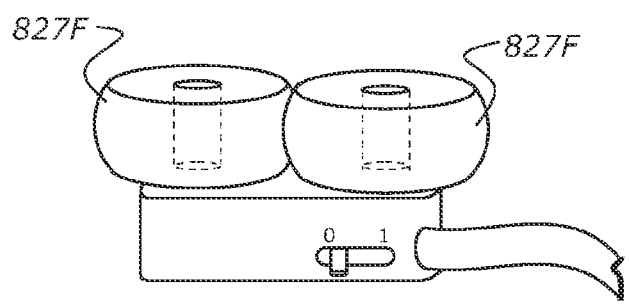

With reference to figures 8e and 8f, another configuration of the user interface is shown. This configuration has prongs 808E that inflate to substantially or completely fill the area of a user's mouth or nose to increase pressure delivery or create a complete seal. The interface has inflatable cuffs 827F that may inflate to fill the gap in the centre, between the prongs, to prevent mouth leak when the interface is inserted into the mouth. The cuffs 827F may be pre-inflated and deflated by a user or clinician or may be initially deflated and inflated by a user or clinician. Alternatively, the cuffs may allow mouth leak by being partially inflated, if desired for example to reduce resistance for expiration. The cuffs may be partially inflated for smaller mouths. The cuffs may be used to increase pressure delivery during nasal therapy. An advantage of this configuration is that the main cannula body can be small as the cuffs are used to create the additional volume that may be necessary to sufficiently occlude the nares to deliver effective therapy.

Figure 8G:
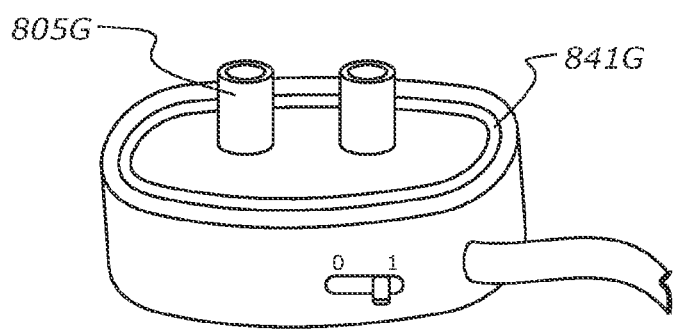
Figure 8H:
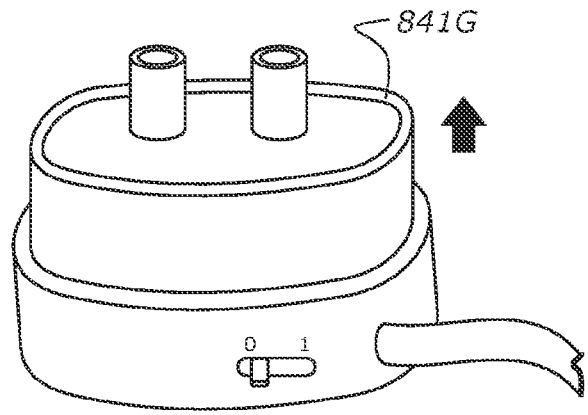

With reference to FIGS. 8g and 8h, another configuration of the user interface is shown. This configuration has an inflatable mouth cuff 841g that rises up off the manifold. The cuff 841g may be pre-inflated and deflated by a user or clinician or may be initially deflated and inflated by a user or clinician. The cuff may also have opening (not shown) to keep the interface unsealed. The cuff can conform to a required shape such as the patient's mouth, which may be more comfortable for the user's mouth and/or may create a better seal in the user's mouth. The cuff may be or comprise a soft, flexible material.

In some configurations described above, the interface may comprise a headgear assembly for locating the interface on the face of the user in-use.

In some configurations, the headgear can be a bifurcated headgear with a pair of rear straps that engage the rear of the patients head. In yet some other configurations the headgear can comprise at least one rear strap to engage the rear of the head or the occiput of the head, and a top strap to engage the top of the user's head.

Where headgear is utilised, the headgear may be configured to provide for a resultant vector force such that the interface, such as the mask, is held on the face with minimal force on the user.

Alternatively, the interface may not comprise any fixing means such as a headgear and a medical practitioner places the interface at a suitable position on a user's face and then gently pushes the interface towards the user's face to sealingly engage the interface with the user's face.

In one embodiment, there is provided a patient interface (not shown) that comprises at least one delivery element 1 for delivering or directing a flow of supplied gas to a nare or the nares of a user's nose, wherein each delivery element 1 comprises of at least one lumen 2 through which said flow of supplied gas is directed, and wherein the flow of supplied gas is modified according to one or more forms 3 that is/are provided within or about an interior of one or more of said at least one lumen 2.

In one embodiment, a patient interface (not shown) including a delivery element 1 provides for a gas flow through a lumen 2 of such a delivery element 1. Such a gas flow can have a turbulent kinetic energy that is the kinetic energy associated with eddies in turbulent flow. Flows with higher levels of turbulence can have a higher skin friction (drag) and therefore require a larger pressure to drive a given flow rate.

Delivery elements may comprise one or more forms, such as which may be one or more of: bumps, ribs, rifling, irregular shaped cross-sections, serrated edges to the delivery element 1, to change whether by increasing or decreasing the level of turbulent kinetic energy being delivered to an airway of a user. In some configurations, an increase or decrease in the pressure generated in the airway may result.

FIG. 9A (a) shows a helical form 3 extending along at least a part of the length of an interior wall surface of a lumen 2 of a delivery element 1.

FIG. 9A (b) shows ridges or longitudinally extending projections as forms 3 along at least a part of the interior wall surface of a lumen 2 of a delivery element 1, this view can also be used as an example of the cross-sectional view of FIG. 9A (c).

FIG. 9A (c) shows lumps or bump type forms 3 positioned in the lumen. These may be positioned in a localised region of a delivery element 1, closer to the outlet of the element 1 than the inlet relative to the direction of flow of supplied gas.

FIG. 9B (a) shows a serrated edge or serrated rim region as a form 3 of a delivery element 1.

FIG. 9B (b) shows the end view of FIG. 9B (c) in which a region toward the end or an outlet of the delivery element 1 includes a generally rippled or corrugated or wavey-type form 3.

FIG. 10A (a) and (b) show an end view and a cross-sectional view of a delivery element 1 that comprises forms 3 as a series or arrangement of partitions in a generally honey-comb or hexagonal type configuration.

FIG. 10B shows forms 3 as a series of partitions in a grid or mesh-like arrangement or array.

FIG. 10C shows forms 3 as a concentric arrangement of walls or partitions, which in this configuration include the optional addition of a bi-secting wall or partition as a further form 3.

Turbulent flows may dissipate more readily than laminar flows. A laminar flow of gases (e.g. a jet type flow) for a given flow rate will therefore likely have a greater penetration depth into the nasal cavity or an airway than a turbulent flow of gases.

In some configurations, a laminar or directional flow of gases may therefore be more advantageous for delivering flow in a targeted manner and delivering a higher pressure to the patient's airway or to lower areas of the patient's airways to reduce the chance of collapse in the airways.

A more laminar flow of gases may be promoted by adding various forms 3, such as flow straighteners to the inside of the delivery element, such as nasal prongs and/or a manifold of a patient interface, such as a nasal cannula. These forms or flow straighteners could be any particular feature that directs the flow into parallel streamlines such as a honey-comb mesh, grid mesh, concentric rings, flow vanes etc. (see FIG. IOa-c). Forms 3 can be used to align the gas flow path as the gas travels through the delivery element 1, and in this way, the gas flow can be directed or focussed so as to achieve such a more laminar or less turbulent type flow.

For example, the forms 3 can be used to channel the gas flow in such a way as to minimise or reduce the likelihood of an increase in turbulence, preferentially in certain situations decreasing the turbulence.

In yet other configurations, the delivery element may be a directionally oriented or angled element with respect to the user or their airway.

For example, in some configurations, relatively higher levels of pressure in the lungs may be created with such relatively high gas flow rates, such as in situations when the flow velocity from the cannula maintained higher for longer. This may be due to a dynamic pressure component of the gas flow, which may translate into an elevated static pressure when the gas flow slows down in different parts of the airway, for example the lower airways.

The Coanda effect, which is the tendency of a fluid flow to attach to a surface can be utilised by having purposefully orientated cannula prongs that direct the flow to be attached to any surface in the nasal cavity or a surface of a user's airway.

A gas flow attached to a nasal cavity or other airway surface is more likely to maintain its high velocity through the nasal cavity or such other airway surface and provide more dynamic pressure following the nasal cavity and the other airway surface and reduce flow dissipation.

In yet further configurations, delivery elements, such as a nasal prong, can be inwardly angled (such as toward a user's septum in-use, or toward a patient's mid-line or sagittal plane), for example in this way the gas flow can attach the flow to the septal wall, inferior angled prongs can attach the flow to the floor of the nasal cavity, and superior angled prongs can attach the flow to the upper surfaces of the nasal cavity. Multiple delivery elements provided in an airway, such as nasal prongs provided in one nostril, can be orientated in different directions may also enhance the pressure delivered (see FIG. 11). FIG. 11 shows two exemplary prong orientations. One orientation is when the prong is angled downwards, that is, an inferior angle. The other orientation is a superior angled prong that attaches flow to the top surface of the nostril.

In other configurations, the delivery element may provide for a gas flow multiplier or multiplication effect.

In some embodiments, for example where the gas flow is a jet-type flow emanating from the delivery element (such as a nasal prong), there can be created a high level of viscous shear on the surrounding air in the atmosphere and inside the airway or a user's nostril. This viscous shear can drag additional room air (or other gases provided to the vicinity of a user's airways, such as the nares of their nose) and into the airway, such as the nasal cavity, along with the flow delivered through the delivery element itself. The shape of the delivery element (e.g. nasal prongs) can be made to enhance this flow multiplier effect to increase the effective flow delivered to the patient. Higher delivered flows can create higher airway pressures. In some cases however the delivery element may be shaped to minimise the flow multiplier effect such that dilution of the gas, such as a warmed and humidified delivered gas, which otherwise supplements colder and dryer room air, is minimised. This is advantageous because gases can be saved and a there may a reduced need for a powerful flow generator to be used.

In yet further configurations, the delivery element may provided for an extended flow pathway into a user's airway. For example, where the delivery element is a nasal prong, relatively long prongs may be employed with a patient interface.

It is desired for the pressure to be transmitted to the lungs, retardation of the flow velocity in the nasal cavity by the nasal resistance reduces the dynamic pressure of the delivered flow and is undesirable. A single long prong or a long prong in each nostril that terminates proximal of the nostril will increase the delivered dynamic pressure as the termination point approaches the lung.

The prongs could for example terminate proximal of the nasal valve (which imposes a large flow resistance) or terminate in the velopharynx (another narrowing that imposes a large flow resistance) such that the flow is targeted directly inferior towards the lungs (in this location a flow multiplier effect may occur as the turbulent flow passes the oral cavity and flow is entrained through the oral cavity). Long prongs may offer the advantages of reduced noise and higher tolerable flow rates since we are bypassing the sensitive nasal epithelia.

The prongs could for example be angled to reduce the back pressure created by restrictions in the airway, such as the nasal valves, and increase the jetting/flow delivery into the lungs. For example, the prongs could be angled so that flow passes centrally through the nasal valve.

The length of the prongs may also be dynamic i.e. they can either automatically or manually grow in length via mechanical or chemical processes i.e. a dial increases their length, they are telescopic, or upon application of humidity, temperature or an electrical current the prong material expands in a longitudinal direction.

In some configurations the prongs may comprise concertina arrangements that are configured to expand the prong (i.e. increase prong length) when there is a high flow rate. Other embodiments may be utilised so as to provide a delivery element 1, such as a nasal prong, with the ability to grow or expand in length dynamically in response to an input (e.g. a characteristic of the gas, such as flowrate or pressure or temperature or humidity or other stimuli such as electrical impedance or other electrical characteristics which may be incorporated into such a delivery element 1).

In yet other configurations, the delivery element may provide for a relatively small area or smaller cross-sectional area of flow path available to the gas as it is transmitted through the delivery element. In situations where the delivery element is one or multiple nasal prongs, such prongs may have a relatively smaller area or a relatively smaller outlet.

Small area prongs can be used to increase the velocity of a given flow exiting the prongs. Small area prongs provided a greater turbulence of airflow and/or pressure in the lower airways of the patient. The increased velocity increases the dynamic pressure and energy of the flow leading to a larger pressure being communicated to the lower airways. The small area prongs with nominally a diameter of less the 30% of the nostril diameter can be used in combination with either turbulators, flow straighteners or directional prongs to achieve higher airway pressures in different cases.

Alternatively, in yet other embodiments, relatively larger area cross-sectional area of the delivery element or an outlet from the delivery element may be provided. In those situations where nasal prongs are utilised, such prongs may have a relatively larger cross-sectional area or outlet.

Large area prongs refer to nasal prongs that substantially fill the nostrils and have a diameter equivalent to about 30%, about 50%, about 70% to about 100% of the nostril diameter, or fill about 30%, about 50%, about 70% to about 100% of the nostril cross-sectional area. By increasing the area of the prong, the flow velocity exiting the prong is reduced for a given flow rate. Therefore, higher gas flow rates could be delivered with a large area prong than a standard nasal prong for the same flow velocity. High velocities may be undesirable in some cases as they could be uncomfortable (noise, vibrations, abrasion) or lead to detrimental effects on sensitive nasal epithelia. High flow rates are desirable in the case of anaesthetic applications in particular (although not limited to) because given the mouth is open, the pressure received by the patient in the lungs is largely flow rate dependant and governed by the oral resistance to flow of the gas flow in turn exiting the mouth. Additionally, large area prongs reduce the leakage area between the prong and the nostril allowing higher pressures to be delivered to the nostrils and subsequently into the lower airways.

In still further configurations, a pressure relief manifold may optionally be incorporated into the patient interface, such as a nasal cannula, circuit or delivery system to ensure a maximum delivered pressure if the mouth is to close during treatment. The pressure relief manifold could be manual or automatic e.g. a port or valve that could be sealed manually using valves or other sealing systems, or through mechanical or electrical operation automatically limit the maximum pressure and/or rate of rise of pressure delivered to the patient. Such seals or valves may also comprises of a one way valve and be used to preferentially deliver pressure on inspiration or expiration. Occluding or occupying a substantial percentage of the nostril area can be achieved in a number of ways, for example:

With reference to FIG. 12, compliant walled prongs 5—Prongs made with a material and/or wall thickness that allows significant stretch for a given applied pressure (compliance) may be used such that the prongs expand to at least substantially fill the nostrils upon application of a flow rate to substantially occlude the nostrils. The prongs may be shaped in such a way to further facilitate this action (e.g. bulge into a balloon shape, see FIG. 12) or include a flow restrictor at the end of the prong to increase the inflating pressure inside the prong. The compliance of the prong walls may be selected such that different levels of compliance provide different levels of nostril occlusion and therefore different pressure ratings.

Prongs that are made from a material that actively or passive expands or grows with the application of humidity, an electrical current, temperature, or other input or parameter such that the prongs substantially fill the nostril area.

In further embodiments, the delivery element, such as nasal prongs, may provided for sealing or non-sealing of the airway into which it or they are to be located.

With reference to FIG. 13, the difference between large area prongs and sealing prongs is that sealing prongs seek to achieve a 100% seal and this may be achieved in combination with a small area prong without necessarily having a large area prong i.e. a small area prong surrounded by an inflatable cuff, 4.

Sealing or optionally sealable prongs on cannula (e.g., inflatable prongs or inflatable outer cuff). Inflatable portion could be connected to actuator on cannula or machine that instantly inflates them from a gas source when additional pressure is desired to create an occlusion with the nares or nostrils of the patient. The inflatable portion could also be connected to a tap off the main gas source (i.e., as the delivered flow rate is increased it is assumed more pressure is desired and the prong seal is increased).

Prongs with an outer inflatable cuff 4 that either expand to fill the nose automatically with flow applied or are inflated with a syringe or another manual or automatic flow or pressure source.

In cases where a perfect seal is not desired (i.e. for comfort or to limit the pressure delivered), ribs may be added to one or both of the outer face of the prongs to ensure a leakage area even when the prongs are fitted into the nostrils with a tight tolerance.

In still further embodiments, the delivery element can include facilities or other accommodation sites or regions to allow for the insertion of other devices into the user's airway or parts of their airway.

Pressure delivery devices such as nasal cannula and masks typically need to be removed to in order to insert nasogastric tubes, bronchoscopes or other airway equipment (e.g. bougie). This leads to an interruption of therapy which can have a significant detrimental effect on the patient. The large area prongs and sealing prongs may include a valve to allow insertion of such a device so that airway pressures can be maintained at an elevated level without interruption. Alternatively, the prongs may seal around the device/instrument 2140, as shown in FIG. 21. Enabling pressure to be delivered during a procedure such as a bronchoscopy also has the advantage of improving airway patency making the bronchoscopy itself easier to perform. FIG. 21 shows a patient interface 2100 having prongs 2105 with cuffs 2127. The cuffs have one or more passages 2141 for receiving the device/instrument 2140. The cuffs may completely seal around the instrument, or partially seal around the instrument.

Relatively high gas flowrates may be utilised in the devices, systems and methods of this disclosure. For example, it may be suitable to provide for gas flowrates of up to about 70 L/min to give significantly longer apnoeic oxygenation times, relative to say about 40 L/min. In combination with a dead space flushing effect, this is likely due to the increased pressure delivered at 70 L/min compared with lower flows. Given that dynamic pressure is proportional to the square of velocity (linearly related to flow rate via Q=VA), a doubled flow rate will lead to four times the pressure delivered.

Accordingly, in combination with one or more of the configurations or embodiments disclosed herein, delivery of flowrates of about 70-200 L/min may be utilised.

Still further embodiments of this disclosure include use of a system for controlling "mouth leak". In an anaesthetic application or other medical procedure, but not solely limited to this, the mouth may be open for the procedure. Pressure delivered via the nose is naturally limited by flow leakage out of the mouth. The leakage of flow out of the mouth during such a procedure may be reduced or eliminated by using an oral insert that controls and/or blocks the leakage flow. The insert may be a mouthpiece. The mouthpiece may be a bite block. The mouthpiece may have relatively large openings that are adapted to receive instruments. This can also create a leakage path for flow delivered to the nostrils.

A mouthpiece may comprise of a hollow opening filled with a membrane and/or valve used to gain access to the airway. Procedural equipment may be able to easily pierce through the membrane, and or pass through the valve and maintain a seal around the mouth and equipment.

A bite block may utilise a spring or other self-opening mechanism between two components to assist in holding the mouth open. Other mouthpieces that engage the patient's mouth may also be used other than a bite block.

The "mouth leak" may be controlled using a mouth piece that partially occludes, partially seals, or completely seals outside the patient's teeth, inside the patient's teeth, outside the patient's lips, inside the patient's lips, and/or partway down the patient's mouth. That is, the mouthpiece may be a two-level occlusion or seal. In yet further embodiments, there is a desire for the maintenance of airway pressure. As outlined herein, it can be advantageous to maintain an elevated airway pressure without interruption. Incorporation of a battery with an anaesthetic specific flow source or a general high flow source of gases is therefore contemplated in order to maintain therapy when a patient or user is being transported from theatre to the recovery room (or from one location to another).

It may be desirable to provide airway pressure via a mask while a nasal cannula is in place. For this case, the nasal cannula gas supply conduit or tubing may be collapsible in the region where the mask contacts the face in order to allow a better seal between the mask and face, facilitating a higher delivered pressure.

In yet other embodiments, there is a desire for pressure control. Contemplated are methods for estimating the pressure delivered to a patient via a patient interface, such as a nasal cannula capable of delivering the relatively high flowrates disclosed herein. It will be appreciated the flow source may need to be automatically or manually adjusted to maintain a delivered airway pressure that meets a prescribed target value or range. This could be controlled electrically or mechanically. Rather than supplying a flow source with a flow control dial (or similar) the dial may allow pressure control and incorporate some safety flow or pressure limits.

It is possible to detect when a patient is asleep and breathing spontaneously (either asleep naturally or under anaesthesia), for example by using particular technology and/or monitoring the respiratory rate and respiratory rate variability via pressure fluctuations in a nasal cannula and/or a system capable of delivering the relatively high flowrates disclosed herein.

In a similar manner it can be detected if anaesthesia has taken affect and paralysed respiration such that the respiratory rate is zero. When a sleep or apnoeic state are detected it may be desirable to automatically increase the flow and pressure delivered to a prescribed or default level.

Given that atelectasis can remain for several hours after surgery and lung collapse reoccurs rapidly after discontinuation of PEEP, it is desirable for an anaesthesia flow source to have a 'recovery' function in which the airway pressure is gradually reduced automatically over time and the patient weaned off to natural breathing. The airway pressure can be reduced by controlling the interfaces to gradually remove the occlusion/seal from the nasal prongs or from the mouthpiece. The length of time of recovery may be inputted and the rate of pressure reduction calculated automatically with a linear or non-linear function or the rate of pressure reduction inputted itself. A default setting may also be used. An indicator (visual, or auditory or even haptic) may be used to show the patient has had their pressure or flow weaned to a desired level.

Disclosed is a lung recruitment device.

A further embodiment relates to an interface used for performing lung recruitment manoeuvres. In one form, the interface comprises a seal which can be selectively activated or used to create or form an occlusion, a partial seal, or a seal, between the user interface and the user's nose and/or mouth. When the occlusion, partial seal, or seal is formed between the interface and the patient's nose and/or mouth, less gas is leaked out of the system which allows a temporary increase in delivered pressure to aid lung recruitment.

FIGS. 14A and 14B show an exemplary embodiment of such interface which comprises a seal 13 which can be selectively activated to create or form an occlusion, partial seal, or complete seal to thereby temporarily increase the pressure delivered to the user. In this example, the interface is a nasal cannula 10 comprising two nasal prongs 12 which extend into nares of a patient when in-use. The prongs 12 generally do not seal against the nares of a patient, which means some gases will be leaked from the prong outlets to the surrounding atmosphere.

In accordance with the disclosures, the nasal prongs 12 each comprise an inflatable seal 13 for example on or surrounding the exterior of the prongs 12. When the seal 13 is in the deflated state, the nasal prongs 12 simply extend into the nares of a patient without forming a seal with the nares of the patient. In the inflated state, the seal 13 inflates, which increases the cross section dimension of the prongs 12 to allow the prongs 12 to seal against the nares and therefore prevent or reduce the gas leakage which would otherwise occur without such sealing arrangement.

In the embodiment shown, the seal activation mechanism comprises a plug 14 which controls the opening and closing of a gas flow path which leads to an interior cavity of the inflatable seal 13. When the gas flow path is open, gas is directed to flow into the seal interior cavity to inflate the seal 13. The plug 14 is biased by a spring 16 to remain in its generally closed position as shown in FIG. 14A. When the plug 14 is pushed down as shown in FIG. 14B, an orifice 15 in the body of the plug 14 aligns with the gas flow path to create an open pathway for the gases. Once the seal is inflated, the plug 14 may return to its generally closed position to keep the gases within the seal 13.

FIG. 17 shows an alternative embodiment that can be selectively activated to create or form an occlusion, partial seal, or complete seal to thereby temporarily increase the pressure delivered to the user. In this embodiment, the interface 1701 may include removable adaptor(s) 1727 to fit over the interface, for example over the prongs 1705. The adaptors may be different sizes to create greater/lesser occlusion and deliver greater/lesser pressure.

FIGS. 18 and 19 shows an alternative embodiment that can be selectively activated to create or form an occlusion, partial seal, or complete seal to thereby temporarily increase the pressure delivered to the user. The prongs 1805 may have tapered portions or components 1827 with increasing cross sectional diameter further from the outlet of the interface (further from the patient). The interface 1801 can be inserted more or less distance into airway to create greater/lesser occlusion.

FIG. 20 shows an alternative embodiment that can be selectively activated to create or form an occlusion, partial seal, or complete seal to thereby temporarily increase the pressure delivered to the user. The interface 2001 may have an adapter in the form of discs or rings 2027 of increasing size further from the outlet of the interface 2001. The discs or rings extend outwardly from the prongs 2005. The interface 2001 can be inserted more or less distance into airway to create greater/lesser occlusion.

Another user interface which may be used as a lung recruitment device is a mouth piece, which may be used separately or in conjunction with the nasal cannula of FIGS. 14A and 14B. FIGS. 15A and 15B show an exemplary mouth piece 17. The mouth piece 17 may be a bite-block. The mouth piece 17 comprises a flange 18 which is to be inserted in the mouth of a user, and which preferably sits behind the teeth of the user when the user closes the mouth; and a biting portion 19, for the user to bite. The biting-portion 19 may be formed into a hollow cylindrical shape or other desirable shape, to allow a tube or other airway devices or instruments to be inserted through a passage 20 formed in the biting portion 19, or just allow the patient to exhale through the mouth piece 17 via the passage 20. The hollow cylindrical shape may be a rigid shape.

In this embodiment, the interior of the passage 20 may also comprise an inflatable seal 22. The seal 22 comprises an associated seal activation mechanism controlling the inflation or deflation of the seal 22. Inflation of the seal 22 closes or at least reduces the size of the passage 20. The mouth piece 17 may use a similar seal activation mechanism such as that used in the nasal cannula of FIGS. 14A and 14B. For example, the seal 22 may be activated by a user pushing a plug 21 in the direction indicated in FIG. 15B. When such mouth piece 17 is used with the nasal cannula of FIGS. 14A and 14B, it prevents or reduces the delivered gas escaping from the mouth which would otherwise reduce the delivered pressure from high flow.

FIGS. 16A and 16B show a different embodiment of a mouth piece 17 which comprises a passage 20 which is selectively closed or at least reduced in size when the seal activation mechanism is activated. The mouth piece 17 has a similar structure as that shown in FIGS. 15A and 15B but uses a different activation mechanism. As shown, the front flange 24 of the mouth piece 17 may comprise a clamp 23 causes the passage 20 to close or reduce in size when it is pushed down into a slot of the front flange.

In some configurations, the interface may include a pressure sensor to display pressure to a user. This may be useful in case of constant delivered flow (e.g., high flow) which will cause increasing pressure as flow is left running into a sealed airway.

Some advantages of the present interfaces are:
  increased pressure delivery helps to improve ventilation/gas exchange by preventing and treating atelectasis and promoting lung recruitment
  the increased occlusion may be implemented in a modular and customisable interface where the occlusion may be increased independently in each of the nares and the mouth: the respiratory support may be delivered through nose and/or mouth
  they allow insertion of instruments without loss of therapy
  they provide partial occlusion of airways, which is advantageous because it prevents atelectasis, prevents alveoli collapse, and/or promote lung recruitment while still providing the benefits of high flow delivery.

The embodiments described herein allow a clinical to increase the pressure delivered to the patient by at least partially occluding some or all of the patient's airways (that is, the patient's nasal passages or mouth) in order to maintain open airways, while still being able to flush $CO_2$ due to using a non-sealing interface with high flow. Additionally or alternatively, a clinician may not activate the seals on any of the interfaces so that high flow gases can be selectively delivered to nose or mouth or both to provide high flow therapy.

In an alternative embodiment, a patient interface may be provided that allows a clinician to selectively supply air to the patient's nose, the patient's mouth, or both the patient's nose and the patient's mouth. This embodiment may comprise detachable prongs and mouthpiece to allow selective delivery of high flow to either the patient's nose, the patient's mouth without applying any occlusion.

The embodiments described herein may provide partial occlusion, partial sealing, or complete sealing. Alternatively, the embodiments described herein may selectively provide gas flow to the patient's nose, the patient's mouth, or both the patient's nose and the patient's mouth without adjustable occlusion or sealing.

The various embodiments disclosed herein may be provided in combination with any one or other of the other embodiments or configurations as disclosed here.

The foregoing description of the disclosure includes preferred forms thereof. Modifications may be made thereto without departing from the scope of the disclosure.

A1. A user interface comprising:
  a nasal cannula having a body portion locatable upon a face of a patient in an operational position, at least one nasal prong extending from the body portion, the nasal prong being adapted to direct a flow of gas into a nare of the patient's nose when the body portion is in the operational position, a port located at or near the body portion, and
  a flow controller for selectively closing the port,
    wherein the port and the flow controller plug are arranged to allow at least part of the flow of gas to vent to control the flow of gas into the nare of the patient's nose from the nasal prong.

A2. A user interface comprising:
  a nasal cannula provided with a cannula gas flow supply,
an oro-nasal mask provided with a mask gas flow supply,
  a port located at or near a body portion of the oro-nasal mask, and a flow controller for selectively closing the port,
    wherein the port and the flow controller are arranged to allow at least part of the flow of gas to vent to control the flow of gas into the patient's airway.

A3. A user interface according to item AI or item A2, wherein the flow controller comprises a removable plug.

A4. A user interface according to item AI or item A2, wherein the flow controller comprises a pressure relief valve.

AS. A user interface according to item AI or item A2, wherein the flow controller comprises an adjustable valve.

A6. A user interface convertible between a nasal configuration, an oral configuration, and an oro-nasal configuration, the user interface comprising:
  a nasal cannula having a body portion, at least one prong extending from the body portion, the prong being adapted to direct a flow of gas into a nare of a user's nose,
  a mouthpiece adapted to direct a flow of gas into a user's mouth, a gas delivery conduit, and
  a valve between the nasal cannula and the mouthpiece, wherein
    in the nasal configuration, the gas delivery conduit delivers a flow of gas to the nasal cannula and the valve prevents or substantially inhibits a flow of gas between the nasal cannula and the mouthpiece,
    in the oral configuration, the gas delivery conduit delivers a flow of gas to the mouthpiece and the valve prevents or substantially inhibits a flow of gas between the nasal cannula and the mouthpiece, and
    in the oro-nasal configuration, the gas delivery conduit delivers a flow of gas to the mouthpiece or the nasal cannula and the valve allows a flow of gas between the nasal cannula and the mouthpiece.

A7. A user interface according to item A6, wherein the nasal cannula and mouthpiece are connected together.

A8. A user interface according to item A6, wherein the nasal cannula and mouthpiece are releasable connected.

A9. A method of providing respiratory support to a patient comprising:
  placing a nasal cannula upon a face of a user in an operational position, the nasal cannula having a body portion and at least one nasal prong extending from the body portion,
  placing an oro-nasal mask upon the face of the user, the oro-nasal mask having a body, said body comprising an aperture or a port allowing for communication of gases to and/or from a gas supply or source to an interior volume of the interface, the interior volume defined by an interior of the body and the face of the user when in-use, a seal provided for creating or forming of a seal between the user interface and the user's face and/or a spacer component provided on the user's face,
  creating or forming of the seal between the mask and the user's face and/or the spacer component so provided on said face, and selectively directing a flow of gas into the user's airway via the nasal prong and/or the oro-nasal mask.

A10. A user interface convertible between a nasal cannula configuration and an oral configuration, wherein:
  in the nasal configuration, the user interface comprises a cannula having a body portion, at least one prong extending from the body portion, the prong being adapted to direct a flow of gas into a nare of a user's nose,
  in the oral configuration, the user interface comprises a cannula having a body portion, at least one prong extending from the body portion, the prong being adapted to direct a flow of gas into a nare of a user's mouth, and a mouthpiece adapted to surround the at least one prong of the cannula and an outer periphery that substantially conforms to the area of a patient's mouth.

A11. A user interface according to item A10, wherein the mouthpiece is clipable onto the cannula.

A12. A user interface according to item A10, wherein the mouth piece is slidable relative to the cannula.

A13. A user interface according to item A10, wherein the prongs are inflatable.

A14. A user interface according to item A10, wherein the mouthpiece is inflatable.

A15. A user interface system comprising a first user interface and a second user interface, the first interface being an unsealed interface and configured for use in conjunction with a second user interface.

B1. A patient interface comprising at least one delivery element for delivering or directing a flow of supplied gas to a nare or the nares of a user's nose, wherein each delivery element comprises of at least one lumen through which said flow of supplied gas is directed, and wherein the flow of supplied gas is modified according to one or more forms is provided within or about an interior of one or more of said at least one lumen.

B2. The interface according to item BI, wherein said form is a, or one more, surface relief portions or regions provided as part of an internal wall surface of one or more of said at least one lumen.

B3. The interface according to item BI or 2, wherein said form is a projection extending radially inwardly from or along an interior wall surface of one or more of said at least one lumen.

B4. The interface according to any one of items BI-3, wherein said form is a depression or recess provided within or along a portion or region of an interior wall surface of one or more of said at least one lumen.

B5. The interface according to any one of items BI-4, wherein said form extends in a continuous or discontinuous manner along or about the delivery element, from a downstream location to a more upstream location, said location being relative to the direction of the flow of supped gas through said delivery element.

B6. The interface according to any one of items BI-5, wherein said form comprises one or more partitions extending along a length and/or across a cross-sectional area of the at least one lumen of a said delivery element.

B7. The interface according to any one of items BI-6, wherein said form is is/are one or more partitions arranged or arrayed in one or a combination of the following:
  substantially concentric configurations, each of said partitions defining at least a part of a further one of said at least one lumen, whether said partitions define a lumen that extends substantially the entirety of the length, or a partial length, of the total length of a delivery element through which said flow of supplied gas is directed,
  a hexagonal or honey-comb type configuration of partitions, whether said partitions defines at least a part of a further one of said at least one lumen, or whether said partitions define a lumen that extends substantially the entirety of the length, or a partial length, of the total length of a delivery element through which said flow of supplied gas is directed,
  a cross-hatch or grid-type arrangement of partitions when viewed as a cross-section through the gas delivery element, the cross-section being taken as a substantially orthogonal plane relative to the direction of the flow supplied gas through the gas delivery element,
  a plurality of intersecting partitions providing plurality of divisions or dividing interior walls within at least one of said lumen of said delivery element,
  a plurality of intersecting partitions providing for a plurality of separate gas flow pathways within at least one of said lumen of a said delivery element,
  one or more partitions are vanes interposed within one or more lumen of said delivery element,
  combinations of one or more of the above arrangements or arrays.

B8. The interface according to any one of items B1-7, wherein said form is/are one or more partitions, a partition being a dividing wall or structure extending through or across a delivery element for gas flow modification or gas flow re-direction.

B9. The interface according to any one of items B1-8, wherein said form imposes upon the flow of gas through one or more regions of one or more delivery elements.

B10. The interface according to any one of items B1-9, wherein said form imposes upon the flow of gas through one or more regions of one or more delivery elements to modify the gas flow by reducing or increasing the Reynolds number of the flow of gas, or at least portions of the flow of gas, through one or more regions of the delivery element.

B10. The interface according to any one of items B1-9, wherein said form imposes upon the flow of gas to increase, or decrease, the kinetic energy of a bulk of the gas flow through the delivery element, or a localised or partial portion of the gas flow through the delivery element.

B11. The interface according to any one of items B1-10, wherein the form comprises a helical structure or surface relief extending from, or imposed upon, an interior wall portion of said at least one lumen of one or more gas delivery elements.

B12. The interface according to any one of items B1-11, wherein the form comprises striations.

B13. The interface according to item B12, wherein said striations are oriented along or with or against a flow direction of supplied gas through a gas delivery element.

B14. The interface according to any one of items B1-13, wherein one or more of said form(s) is/are located in one or more of:
  in a portion or region closer to an outlet from the delivery element than an inlet of the supplied gases to the delivery element,
  in a portion or region closer to an inlet to the delivery element than an outlet of the supplied gases from the delivery element,
  in a portion or region comparatively more downstream than an upstream portion or region of a delivery element relative the flow of gas supplied,
  in a portion or region comparatively more upstream than a downstream portion or region of a delivery element relative the flow of gas supplied,
  at or substantially adjacent to an outlet (or an end) from the delivery element of the supplied gases,
  an outlet end of the delivery element.

B15. The interface according to any one of items B1-14, wherein an outlet end of said delivery element comprises the form as one or a serried of serrated surfaces or undulating shaped or castellated edge portions.

B16. The interface according to any one of items B1-15, wherein said form is one or more ribs provided substantially longitudinally aligned with a gas flow direction through the delivery element, or said one or more ribs is/are provided substantially laterally (or another orientation) substantially relative to a gas flow direction through the delivery element.

B17. The interface according to any one of items B1-16, wherein said form is of a regular or irregular geometry, when viewed as a cross-sectional profile or as plan view of a surface of a delivery element including such a said form or forms.

B18. The interface according to any one of item B1-17, wherein the, or one or more of said, form(s) is/are gas flow directors.

B19. The interface according to item B18, wherein a said form straightens or directs the gas flow into a flow path trajectory or other gas flow characteristic.

B20. The interface according to any one of items B1-19, wherein said form straightens said gas flow or provides or alters said gas flow as a jet or focussed flow of gas through or from said delivery element or through or from at least one of said lumen through a delivery element.

B21. The interface according to any one of items B1-20, wherein said form operates as a gas flow multiplier for increasing the flowrate of provided to a user, the gas flowrate provided to a user being greater than the total gas flowrate delivered through the delivery element of a said interface.

B22. The interface according to any one of items B1-21, wherein said delivery element is oriented or angled, such that in-use, said delivery element is oriented or angled toward a user's septum.

B23. The interface according to any one of items B1-22, wherein a said delivery element extends to, or substantially adjacent to, in-use, one of:
  a user's nasal valve
  the velopharynx
  sufficiently deep into a user's airway or nasal cavity, so s to in-use, avoid or by-pass gas flow being provided in contact with a user's relatively sensitive nasal epithelia.

B24. The interface according to any one of items B1-23, wherein a delivery element extends in flowpath length, whether automatically in response to a characteristic of the supplied gas or by manually actuation.

B25. The interface according to any one of items B1-24, wherein said delivery element is telescopic.

B26. The interface according to any one of items B1-25, wherein said delivery element responds to a change in temperature or a change in humidity or an electrical current applied thereto.

B27. The interface according to item B26, wherein said response is an alteration or change in the geometry or flowpath of a said delivery element.

B28. The interface according to any one of items B1-27, wherein an outlet from a delivery element is shaped or configured to change the velocity of gas exiting said delivery element.

B29. The interface according to item B28, wherein said velocity (whether as a bulk property or a localised property of said supplied gas passing through or exiting a said delivery element) is increased or decreased.

B30. The interface according to any one of items B1-29, wherein said form is a flow restrictor.

B31. The interface according to any one of items B1-30, wherein said delivery element is of a non-sealing type relative to an airway or a nasal cavity or nare into which said delivery element is to be located, optionally such that the nare or airway that said delivery element is to be located within does not occlude the entire airway or a nare when in-situ.

B32. The interface according to any one of items B1-31, wherein said delivery element further comprises one or more structures positioned on an exterior surface of said delivery element, such that, in-use, said a sealing of said delivery element with an airway or a nare when in-use, is dissuaded or avoided or prevented.

B33. The interface according to any one of items B1-30, wherein said delivery element is of a sealing-type, optionally wherein the delivery element occludes or seals the airway or nare when in-situ.

B34. The interface according to item B33, wherein said delivery element further comprises one or more structures positioned on an exterior surface of said delivery element, such that, in-use, said a sealing of said delivery element with an airway or a nare when in-use, is encouraged.

B35. The interface according to item B34, wherein said structure(s) comprises one or more inflatable members for encouraging of said sealing, optionally said member being at least one inflatable cuff.

B36. The interface according to item B35, wherein the inflatable member is inflated to a pressure proportional to the pressure of the supplied gas or to a pressure correlated to the pressure of the supplied gas.

B37. The interface according to item B35 or 36, wherein said inflatable member is inflated by the supplied gas.

B38. The interface according to item B35 or 36, wherein said inflatable member is inflated by a source of gas other than the supplied gas.

B39. The interface according to any one of items B35-38, wherein the inflatable member is manually inflated by a user, or is automatically inflated, such as in response to a supplied source of gas.

B40. The interface according to any one of items B1-39, wherein said delivery element further comprises an accommodation to allow for insertion of an instrument or tube or conduit or other airway equipment, including a bougie, into a said delivery element to access a user's airway, such as a nasal cavity or nare.

B41. The interface according to any one of items B1-40, wherein said delivery element is a nasal prong.

B42. The interface according to any one of items B1-41, wherein said interface is a nasal cannula including one or a pair of nasal prongs.

B43. The interface according to any one of items B1-42, when provided as a nasal cannula comprising one or a pair of nasal prongs as said delivery elements, in combination with a further patient interface when provided as an oro-nasal or full-face type mask, optionally each of said patient interfaces supplied separately with a source of gas to their gas outlet from respective delivery elements.

B44. The interface according to any one of items B1-43, wherein the or an interface or a component associated with a system for providing a supply of gas to said interface, includes a pressure relief mechanism.

B45. The interface according to item B44, wherein the pressure relief mechanism is a valve or other seal configured to open once a pre-determined pressure is experienced or sensed within a delivery element or at a location along a gas flow path of the gas supplied to the interface or a said gas delivery element, or said pre-determined pressure is measured or sensed at another location external to the interface of the system for providing the supply of gas.

The invention claimed is:

1. A user interface for providing a flow of respiratory gases to a patient during a medical procedure comprising:
  a nasal interface comprising a body and a pair of prongs extending from the body, the prongs configured to engage nares of a patient's nose and direct high flow respiratory gases into the nares;
  a mouthpiece adapted to engage a patient's mouth;
  wherein the mouthpiece is inflatable;
  wherein the prongs and/or the mouthpiece are configured to at least partially occlude either an oral airway, a nasal passage, or both the oral airway and the nasal passage in use;
  wherein the mouthpiece comprises a passage to allow insertion of a medical instrument through the mouthpiece;
  wherein the passage is selectively openable and closeable to seal around the medical instrument inserted through the mouthpiece; and
  wherein the user interface is adapted to allow a user to selectively create at least a partial occlusion with a patient's nares, a patient's oral airway, or both.

2. The user interface of claim 1, wherein the prongs are configured to create at least a partial seal with a patient's nares.

3. The user interface of claim 1, wherein the mouthpiece is configured to create at least a partial seal with the patient's mouth or a patient's oral airway.

4. The user interface of claim 1, wherein the prongs are shaped to create a seal with a patient's nares.

5. The user interface of claim 1, wherein the mouthpiece is shaped to create a seal with the patient's mouth or a patient's oral airways.

6. The user interface of claim 1, wherein the mouthpiece is arranged to direct a high flow respiratory gases into the patient's mouth or a patient's oral airways.

7. The user interface of claim 6, wherein the high flow respiratory gases are greater than 20 L/min.

8. The user interface of claim 6, wherein the high flow respiratory gases are humidified.

9. The user interface of claim 1, further comprising a mechanical control mechanism that allows selective inflation of the mouthpiece.

10. The user interface of claim 1, wherein the nasal interface is removably connectable to the mouthpiece.

11. The user interface of claim 1, wherein the mouthpiece is inflatable when the nasal interface is connected to the mouthpiece.

12. The user interface of claim 1, wherein the mouthpiece comprises an outer inflatable seal that is adapted to inflate to create a seal with the patient's mouth.

13. The user interface of claim 1, further comprising a seal activation mechanism controlling an inflation and deflation of the mouthpiece and/or wherein the mouthpiece comprises a valve that can be selectively opened or closed based on a patient's inspiration and/or a patient's expiration.

14. The user interface of claim 1, wherein the flow of respiratory gases to the patient is humidified.

15. The user interface of claim 1, wherein the flow of respiratory gases are provided to the nasal interface through a single side entry to the nasal interface.

16. The user interface of claim 1, wherein the flow of respiratory gases is a high flow of respiratory gases that is greater than 20 L/min.

17. A user interface for providing a flow of respiratory gases to a patient during a medical procedure comprising:
a nasal interface comprising a body and a pair of prongs extending from the body, the prongs configured to engage nares of a patient's nose and direct high flow respiratory gases into the nares;
a mouthpiece adapted to engage a patient's mouth;
wherein the mouthpiece is inflatable;
wherein the prongs and/or the mouthpiece are configured to at least partially occlude either an oral airway, a nasal passage, or both the oral airway and the nasal passage in use;
wherein the mouthpiece comprises a passage to allow insertion of a medical instrument through the mouthpiece;
wherein the passage comprises a passage inflatable seal, the passage inflatable seal being adapted to seal around a medical instrument inserted into the passage; and
wherein the user interface is adapted to allow a user to selectively create at least a partial occlusion with a patient's nares, a patient's oral airway, or both.

* * * * *